(12) United States Patent  (10) Patent No.: US 8,211,036 B2
Schraga  (45) Date of Patent: Jul. 3, 2012

(54) DISPOSABLE LANCET DEVICE CAP WITH INTEGRAL LANCET AND/OR TEST STRIP AND TESTING DEVICE UTILIZING THE CAP

(75) Inventor: Steven Schraga, Surfside, FL (US)

(73) Assignee: STAT Medical Devices, Inc., North Miami, FL (US)

( * ) Notice: Subject to any disclaimer, the term of this patent is extended or adjusted under 35 U.S.C. 154(b) by 1793 days.

(21) Appl. No.: 11/138,277

(22) Filed: May 27, 2005

(65) Prior Publication Data

US 2006/0271084 A1 Nov. 30, 2006

(51) Int. Cl.
*A61B 5/00* (2006.01)
*B65D 81/00* (2006.01)

(52) U.S. Cl. ........................ 600/583; 600/573

(58) Field of Classification Search ................ 600/300, 600/306, 372, 382, 384, 573, 583, 584; 606/167, 606/170, 172, 181, 182, 184, 185
See application file for complete search history.

(56) References Cited

U.S. PATENT DOCUMENTS

| | | | |
|---|---|---|---|
| 4,895,147 A | 1/1990 | Bodicky et al. |
| 5,035,704 A | 7/1991 | Lambert et al. |
| 5,201,324 A | 4/1993 | Swierczek |
| 5,395,388 A | 3/1995 | Schraga |
| 5,643,306 A | 7/1997 | Schraga |
| 5,971,941 A | 10/1999 | Simons et al. |
| 6,228,100 B1 | 5/2001 | Schraga |
| 6,464,649 B1 | 10/2002 | Duchon et al. |
| 6,506,168 B1 | 1/2003 | Fathallah et al. |
| 7,299,081 B2 | 11/2007 | Mace et al. |
| 2002/0169470 A1 | 11/2002 | Kuhr et al. |
| 2002/0198444 A1 | 12/2002 | Uchigaki et al. |
| 2003/0050573 A1 | 3/2003 | Kuhr et al. |
| 2003/0083686 A1 | 5/2003 | Freeman et al. |
| 2003/0225430 A1 | 12/2003 | Schraga |
| 2004/0023625 A1 | 2/2004 | Jonsson |
| 2004/0092995 A1 | 5/2004 | Boecker et al. |
| 2004/0230216 A1 | 11/2004 | Levaughn et al. |
| 2004/0236251 A1 | 11/2004 | Roe et al. |
| 2004/0260325 A1 | 12/2004 | Kuhr et al. |
| 2005/0021066 A1 | 1/2005 | Kuhr et al. |
| 2005/0118071 A1 | 6/2005 | Sacherer |
| 2005/0277850 A1 | 12/2005 | Mace et al. |
| 2006/0224172 A1 | 10/2006 | Levaughn et al. |

FOREIGN PATENT DOCUMENTS

CN 1407871 4/2003
WO WO 2005/018710 3/2005

OTHER PUBLICATIONS

U.S. Appl. No. 10/988,636, in the name of Schraga, filed Nov. 16, 2004.
U.S. Appl. No. 11/035,978, in the name of Schraga, filed Jan. 18, 2005.
U.S. Appl. No. 11/073,736, in the name of Schraga, filed Mar. 8, 2005.

*Primary Examiner* — Jeffrey G Hoekstra

(74) *Attorney, Agent, or Firm* — Greenblum & Bernstein, P.L.C.

(57) ABSTRACT

Cap for a testing device. The cap includes a lancet movably mounted within the cap and a skin-engaging end having an opening that allows a portion of a needle of the lancet to pass therethrough. A test strip may be arranged on the cap. This Abstract is not intended to define the invention disclosed in the specification, nor intended to limit the scope of the invention in any way.

49 Claims, 25 Drawing Sheets

DISPOSABLE LANCET DEVICE CAP WITH INTEGRAL LANCET AND/OR TEST STRIP AND TESTING DEVICE UTILIZING THE CAP

BACKGROUND OF THE INVENTION

1. Field of the Invention

The invention relates to a disposable lancet device cap which includes a test strip and a lancet or lancet needle. The invention also relates to a disposable cap for a testing device such as glucose meter. The invention further relates to a method of using a testing device such as a blood glucose meter with a removable/replaceable cap. In particular, the invention relates to a cap having both a lancet needle and a test strip which may be disposable, i.e., which can be used once and discarded, and/or which utilizes an arrangement which protects a user from contacting his or her skin with needle after the testing device has been triggered and/or fired.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Known single-use/disposable lancet devices are not sufficiently and/or properly design to ensure that they cannot be reused. Moreover, such devices generally do not protect a user from coming into contact with the needle after the device has been used. Known testing devices such a glucose meters do not utilize a disposable cap which includes an integrally mounted lancet needle and/or a test strip.

An improved device would allow the user to use the lancet needle only a single time and more reliably and safely prevent reuse of the lancet needle. The device should also ensure that a contaminated needle cannot come into contact with a user after the device is used or triggered. Finally, an improved device would utilize a disposable cap which is safe to dispose of, is simple in design, and is inexpensive to produce.

SUMMARY OF THE INVENTION

According to one illustrative aspect of the invention there is provided a disposable lancet device cap for a testing device or glucose meter.

The invention also provides a cap for a testing device, wherein the cap comprises a lancet movably mounted within the cap and a skin-engaging end having an opening that allows a portion of a needle of the lancet to pass therethrough.

The cap may be structured and arranged to be removably mounted to the testing device. The opening may be less than approximately 10 times a diameter of the needle. The opening may be less than approximately 5 times a diameter of the needle. The opening may be less than approximately 3 times a diameter of the needle. The opening may be less than approximately 2 times a diameter of the needle.

The cap may further comprise an open end adapted to be removably connected to the testing device.

The cap may further comprise a mechanism for ensuring that the cap is mounted to the testing device in a single rotational position.

The cap may be structured and arranged to be non-rotationally removably mounted to the testing device. The cap may comprise a generally cylindrical side wall. The cap may include an arrangement for automatically retracting or moving the lancet to the retracted position after the lancet moves to the extended position.

The cap may further comprise a test strip having one end extending to the opening.

The cap may further comprise a test strip having one end extending to the opening and another end extending along a side wall of the cap.

The cap may further comprise a test strip at least partially arranged on an outer surface of the cap.

The cap may further comprise a test strip having contacts arranged on a side wall of the cap.

The cap may further comprise a test strip having contacts arranged in an area of the opening.

The cap may further comprise a mechanism for retaining the cap on the testing device.

The cap may further comprise an arrangement for adjusting a penetration depth of the needle of the lancet.

The cap may be disposable. The mechanism may comprise a projection. The mechanism may comprise an inwardly facing circumferential projection.

The cap may further comprise an arrangement for biasing the lancet towards a retracted position. The arrangement may comprise a spring. The arrangement may comprise at least one member connected to a portion of the cap via a living hinge.

The cap may further comprise an arrangement for retaining the lancet in a retracted position.

The arrangement for retaining the lancet in a retracted position may comprise at least one projection arranged on the lancet and at least one projection non-movably connected to the cap. The arrangement for retaining the lancet in a retracted position may comprise at least one projection arranged on the lancet and at least one projection integrally formed with the cap. The arrangement for retaining the lancet in a retracted position may comprise at least one projection arranged on the lancet and at least one projection arranged on an inner side wall of the cap. The arrangement for retaining the lancet in a retracted position may comprise at least one circumferential projection arranged on the lancet and at least one circumferential projection arranged on an inner cylindrical side wall of the cap.

The invention also provides a testing device comprising the cap described above, wherein the testing device comprises a body and a display.

The invention also provides a testing device comprising the cap described above, wherein the testing device comprises a body, a display, and a triggering system.

The invention also provides a testing device comprising the cap described above, wherein the testing device comprises a body, a display, and a mechanism for making electrical contact with a portion of the cap.

The invention also provides a testing device comprising the cap described above, wherein the testing device comprises a body, a display, a triggering system, and contacts for making electrical contact electrical contacts of the cap.

The invention also provides a method of puncturing a surface of skin using a testing device comprising the cap described above, wherein the method comprises arranging the skin-engaging end adjacent against a user's skin, triggering the testing device so that the needle is caused to puncture the user's skin, testing fluid from the puncture, and removing the cap and installing a new cap on the testing device.

The invention also provides a disposable cap for a testing device, wherein the cap comprises a lancet movably mounted within the cap, a skin-engaging end having an opening that allows a portion of a needle of the lancet to pass therethrough, and a test strip for testing a fluid in an area of the opening.

The cap may be structured and arranged to be removably mounted to the testing device. The opening may be less than approximately 5 times a diameter of the needle.

The cap may further comprise an open end adapted to be removably connected to the testing device.

The cap may further comprise a mechanism for ensuring that the cap is mounted to the testing device in a single rotational position.

The cap may be structured and arranged to be non-rotationally removably mounted to the testing device. The test strip may be at least partially arranged on an outer surface of the cap.

The cap may further comprise a mechanism for retaining the cap on the testing device.

The cap may further comprise an arrangement for biasing the lancet towards a retracted position.

The cap may further comprise an arrangement for retaining the lancet needle in a retracted position.

The invention also provides for a testing device comprising the cap described above, wherein the testing device comprises a body and a display. The testing device may comprise may comprise the cap described above and a body, a display, and a triggering system. The testing device may comprise the cap described above and a body, a display, and a mechanism for making electrical contact with the test strip. The testing device may comprise the cap described above and a body, a display, a triggering system, and contacts for making electrical contact electrical contacts of the test strip.

The invention also provides a method of puncturing a surface of skin using a testing device described above, wherein the method comprises arranging the skin-engaging end adjacent against a user's skin, triggering the testing device so that the needle is caused to puncture the user's skin, testing fluid from the puncture, and removing the cap and installing a new cap on the testing device.

The invention also provides a disposable cap for a testing device, wherein the cap comprises a lancet movably mounted within the cap, an arrangement for biasing the lancet towards a retracted position, a skin-engaging end having an opening that allows a portion of a needle of the lancet to pass therethrough, and a test strip for testing a fluid in an area of the opening.

The invention also provides a glucose meter comprising the disposable cap described above.

The invention also provides method of testing a fluid sample using the glucose meter described above, wherein the method comprises arranging the skin-engaging end adjacent against a user's skin, triggering the glucose meter so that the needle is caused to puncture the user's skin, testing fluid from the puncture, and removing the cap and installing a new cap on the glucose meter.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
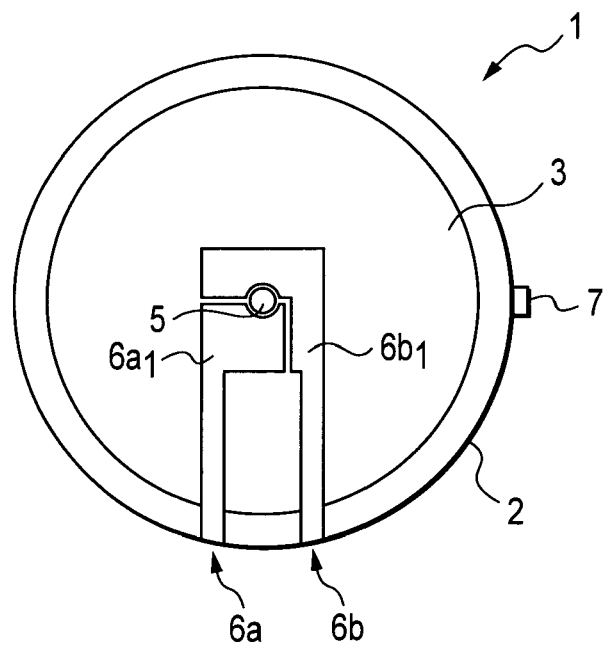
FIG. 1 shows a top or end view of one embodiment of the cap. The contacts of the test strip is shown surrounding the lancet needle opening and to extend to the side wall.
Figure 2:
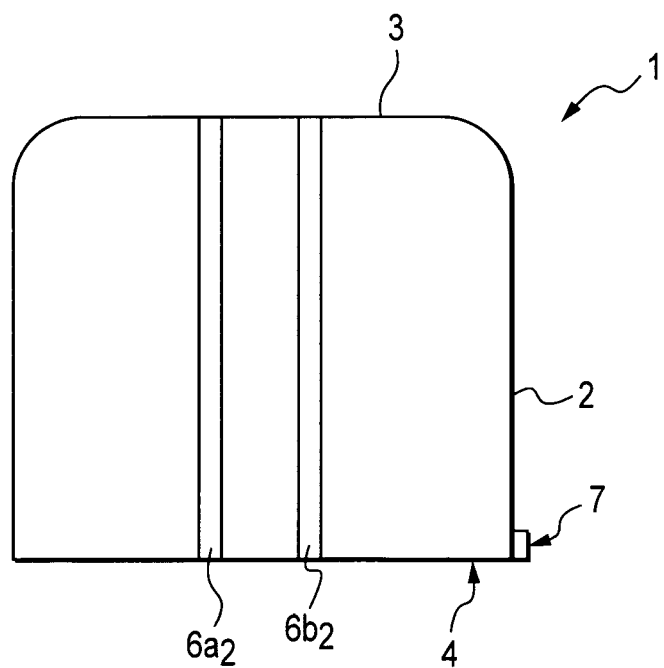
FIG. 2 shows a side view of the cap of FIG. 1.

FIGS. 1-4 show a first non-limiting embodiment of a cap 1. The cap 1 is preferably made of a synthetic resin material and can have any desired shape. In the illustrated embodiment, the cap 1 has a generally cylindrical shape including a generally cylindrical side wall 2 which extends between a skin-engaging wall 3 and an open end 4. The skin-engaging wall 3 includes an opening 5 which is sized to allow a needle N to pass therethrough. The cap 1 also includes a test strip which is at least partially arranged on an outer surface of the cap 1. Preferably, the test strip is of conventional design and can be laminated or otherwise adhered or secured to an outer surface of the cap 1. As can be seen in FIGS. 1 and 2, the test strip includes two thin contact leads 6a and 6b which have upper exposed contacts or ends 6a1 and 6b1 and lower exposed contacts or ends 6a2 and 6b2. The exposed contacts 6a1 and 6b1 are arranged an area of the opening 5 in order to record blood or other body fluid which results from a puncture by the needle N. Such puncturing occurs when the skin-engaging wall 3 is placed against a user's skin (after the cap 1 is placed on a testing device) and the testing device triggered. The lower exposed contacts 6a2 and 6b2 are arranged an area of the opened end 4 in order to ensure that electrical contact is made with corresponding contacts on the testing device, as will be described in detail later on. Although not shown, the skin engaging wall 3, or the surface thereof, need not be planar, and can also be either slightly concave or slightly convex. The skin-engaging surface can also include features known in the art such as projections, for, e.g., stimulating blood flow or otherwise limiting the amount of any pain which results from the puncture. The cap 1 also includes a projection 7 for ensuring that the cap 1 is installed onto the testing device in only a single position. This ensures that the exposed contacts 6a2 and 6b2 are correctly aligned and make contact with corresponding contacts of the testing device.

Figure 3:
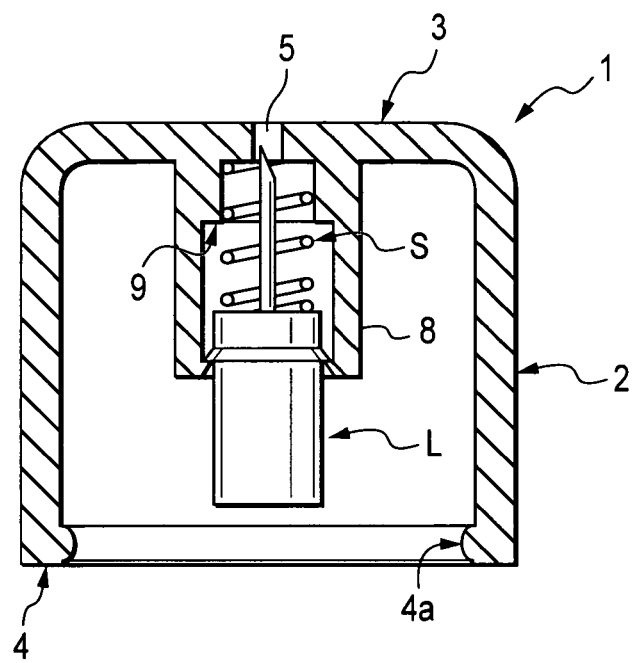
FIG. 3 shows a cross-section view of the cap shown in FIG. 2.
Figure 4:
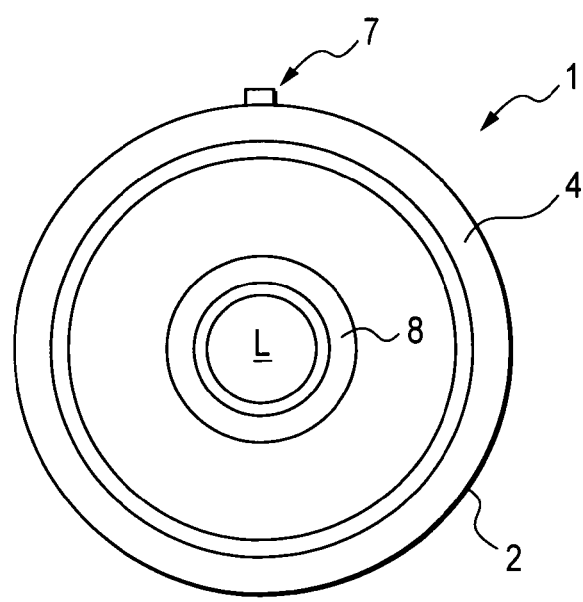
FIG. 4 shows a bottom view of the cap of FIG. 1.

As can be seen in FIGS. 3 and 4, the cap 1 further includes an integrally formed inner housing within which a lancet L is movably mounted. The housing is formed by a generally cylindrical wall 8 which has a bottom opened end and an upper end which extends to the wall 3. A spring S is arranged within the housing in order to bias the lancet N towards a retracted position. The spring S ensures that after the lancet L is moved to a fully extended position (see FIG. 8), the lancet L is moved automatically back to the retracted position (see FIG. 3). The housing also includes a stop shoulder 9 which is contacted by the upper or needle end of the lancet L when the lancet L moves to the extended position (see FIG. 8). The particular location of the stop shoulder 9 can be "factory" set to produce a particular pre-determined penetration depth. According to one non-limiting aspect of the invention, the cap 1 can be labeled with indicia indicating the set depth so that the user will know, when the cap 1 is installed on a testing device, that it will produce the indicated puncture depth. Thus, a user having thicker skin may desired to procure a cap for his or her testing device which contains indicia indicating that the cap is a "deep" penetration cap. A user having somewhat thinner skin may desire to procure a cap for his or her testing device which contains indicia indicating that the cap is a "intermediate" penetration cap. Finally, a user having thin skin may desire to procure a cap for his or her testing device which contains indicia indicating that the cap is a "shallow" penetration cap.

Figure 5:
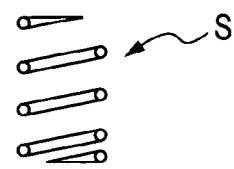
FIG. 5 shows a cross-section view of the spring used in the cap shown in FIGS. 1-4.
Figure 6:
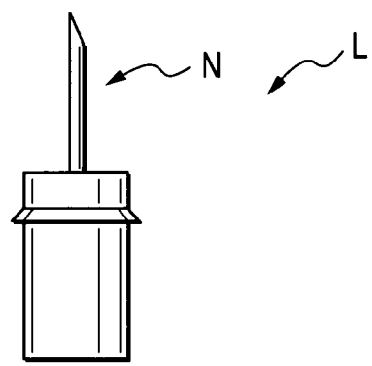
FIG. 6 shows a side view of the lancet shown in the cap of FIGS. 1-4.
Figure 7:
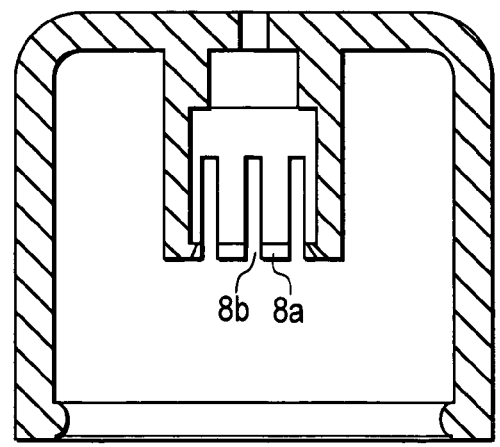
FIG. 7 shows a cross-section view of the cap shown in FIG. 3, but with the spring and lancet removed therefrom.

As can be seen in FIG. 3, the generally cylindrical wall 8 is designed to ensure that once the lancet L is inserted into the inner housing, it is prevented from being removed. FIGS. 5 and 6 show the spring S and the lancet L removed from the cap 1. FIG. 7 shows that the lower or open end of wall 8 is formed by a plurality of fingers which define an inwardly facing tapered projection 8a separated by a plurality of slots 8b. The fingers forming the wall 8 can flex outwardly to allow the lancet L to be inserted in the inner housing. Of course, the spring S is inserted prior to insertion of the lancet L. As is evident from FIG. 6, when the tapered circumferential projection of the lancet L slidably engages the tapered projection 8*a*, the fingers are caused to deflect outwardly until the lancet L is inserted sufficiently into the inner housing to assume the position shown in FIG. 3. The lancet L can be made of conventional materials which are used to make lancets. Preferably, the lancet L is made by injection molding with the needle N positioned therein in order to produce a lancet which is of low cost. The spring S can be made of any desired material and is preferably made of spring steel such as, e.g., stainless steel. By way of non-limiting example, the cap 1 can have an outer diameter of between approximately 0.25" and 1" and is preferably between approximately ½" and ¾" in diameter. The cylindrical portion of the lancet L can be between approximately ⅛" and ¼" and can be made of a synthetic resin material. The spring S can be of any desired type and can preferably be a wire compression spring. The test strip can be in the range of between approximately 0.15 and approximately 0.25 in width, approximately 0.015" and approximately 0.05" in thickness and between approximately 0.5" and approximately 1.25" long.

Figure 8:
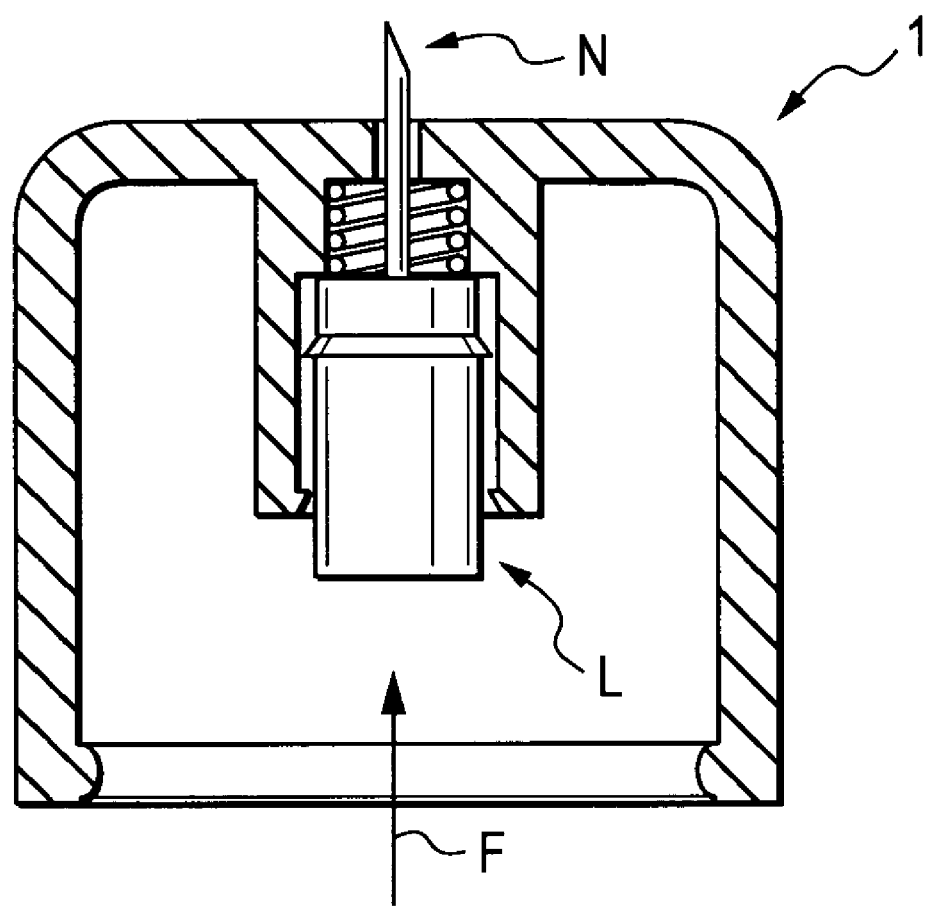
FIG. 8 shows a cross-section view of the cap in FIG. 3 after the lancet has been moved or forced to the extended position.

As can be seen when comparing FIGS. 3 and 8, the lancet L moves linearly and/or axially within the inner housing of the cap 1 between a retracted position (FIG. 3) and an extended position (FIG. 8). This movement occurs as a result of a force F being applied to the lancet L. The force F is preferably applied by a plunger or other activating member that is part of a testing device. In this way, when the cap 1 is mounted to the testing device, and the user triggers the testing device (or otherwise causes a plunger in the testing device to engage the lancet L), the lancet L is caused to move to the extended position from the retracted position. The force F, of course, must be greater than the biasing force of the spring S in order to cause the lancet L to move to the fully extended position. As explained above, the maximum movement of the lancet L (which controls the amount of the tip or the needle N that projects from, past or beyond the skin-engaging surface of wall 3) within the inner housing is determine or set by contact between the upper end of the lancet body and the shoulder 9. Although not shown, the lancet L can include a device that prevents the lancet L from rotating within the inner housing. This device can be, e.g., a projection which slidably engages a slot in the wall 8. Alternatively, the slot can be arranged on the lancet L and the projection can be arranged on the inner cylindrical surface of the wall 8. Still another way to ensure that the lancet L does not rotate within the inner housing, if such an arrangement is desired, is to replace the generally cylindrical body of the lancet L with one that has, e.g., generally oval, or triangular, or square, or polygonal shaped cross-section. Of course, the shape of the space within the inner housing should preferably correspond to the shape of the lancet L. There also should be some amount of clearance between the lancet body and the inner surface of the wall 8 to allow the lancet L to move freely within the inner housing.

Figure 9:
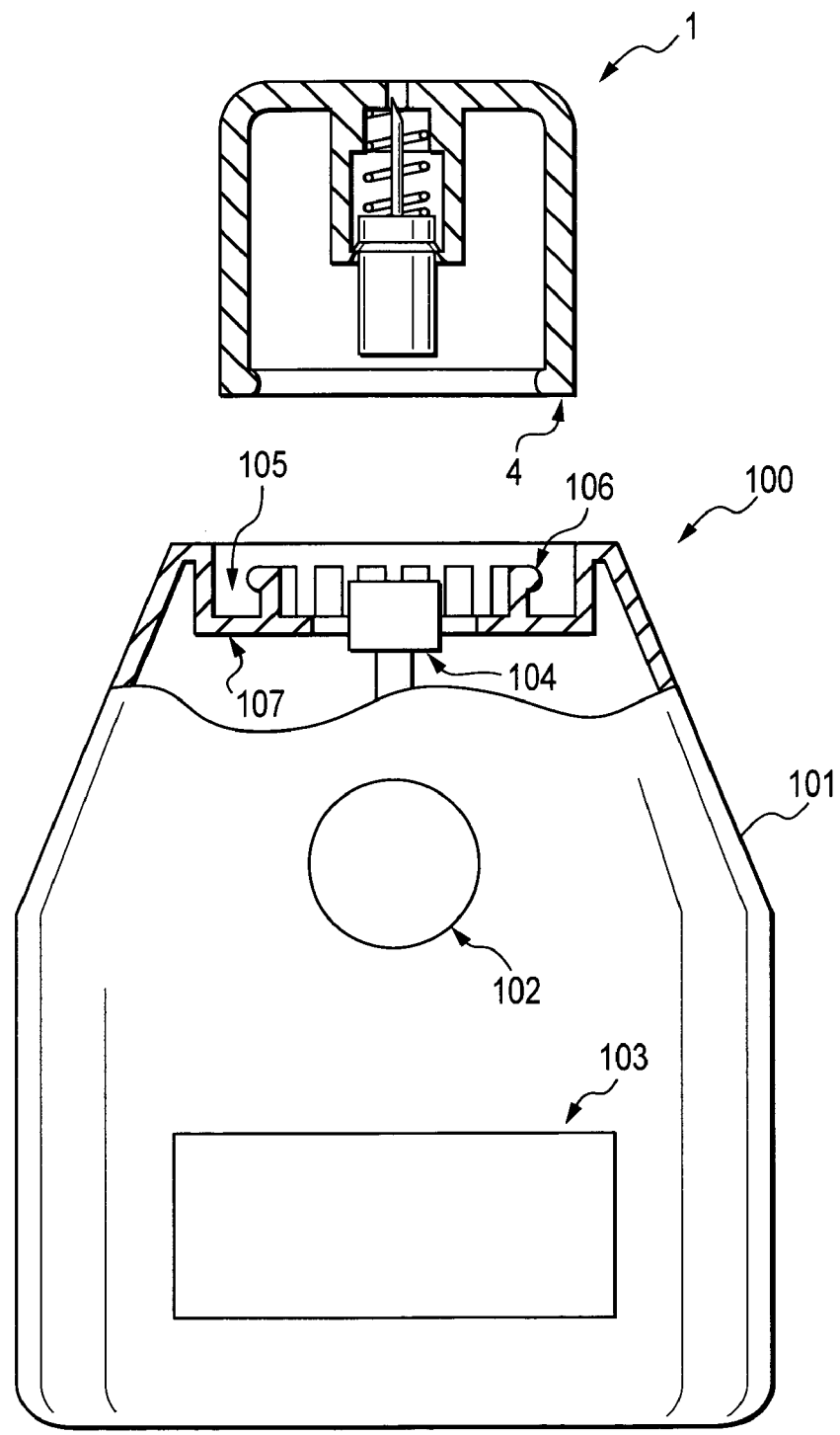
FIG. 9 shows side view of the cap shown in FIG. 3 arranged above one embodiment of a testing device, which is shown in partial cross-section. The electrical contacts of the testing device are not shown.

FIG. 9 shows one non-limiting embodiment of a testing device 100 which can utilize the cap 1. Preferably, the testing device 100 has a body 101 which can be made of synthetic resin. A trigger button 102 is arranged on the body 101 in order to trigger movement of a plunger 104. The testing device 100 also includes a display 103 in order to provide the user with information such as, e.g., blood glucose value or other information related to a fluid sample, that is measured with the test strip of the cap 1. The testing device may be of conventional design and include all of the electronic circuits and devices generally utilized with conventional glucose meters. However, the testing device further requires an arrangement which allows the cap 1 to be removably secured thereto. Such an arrangement can have the form of a recessed area 105 which is sized to receive therein the open end 4 of the cap 1. The arrangement can also include a circumferential projection 106 which is designed to releasably engage the projection 4*a* of the cap 1. The circumferential projection 106 is arranged on a plurality of axially arranged fingers which extend from a wall 107 of the testing device 100. In order to ensure that the plunger 104 can pass through the wall 107, an opening 108 (see also FIG. 10*b*) is sized to be larger than a maximum diameter of the plunger 104 and is provided in the wall 107. The opening 108 is preferably generally centrally disposed relative to the projection 106 in order to ensure that the plunger 104 is properly aligned with the lancet L of the cap 1.

Figure 10A:
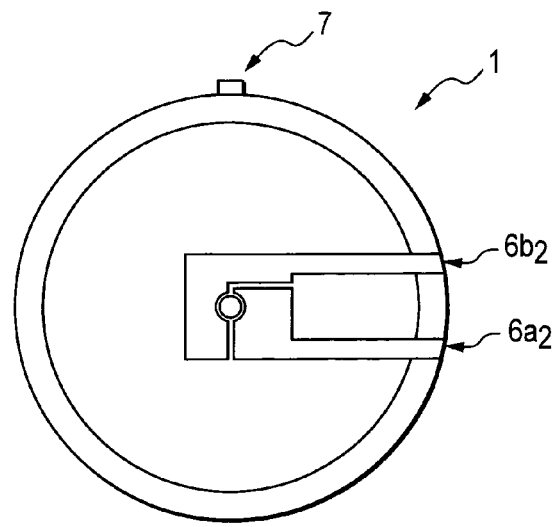
FIG. 10a shows a top view of the cap shown in FIG. 1 prior to being installed on the testing device shown in FIGS. 9 and 10b.
Figure 10B:
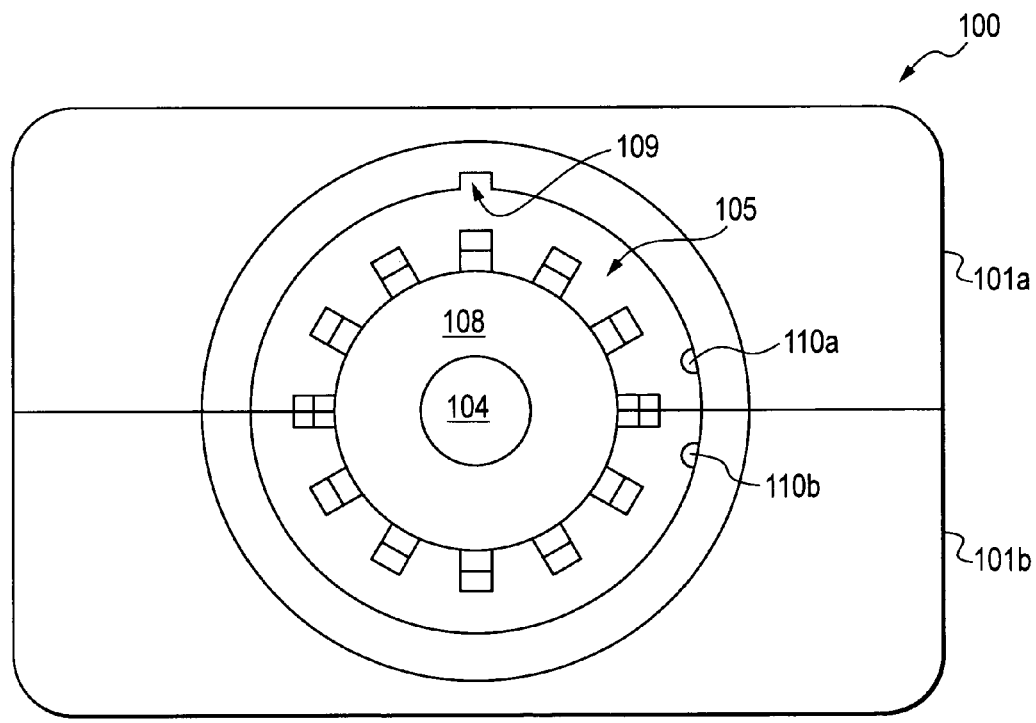
FIG. 10b shows a top view of the testing device of FIG. 9.
Figure 11:
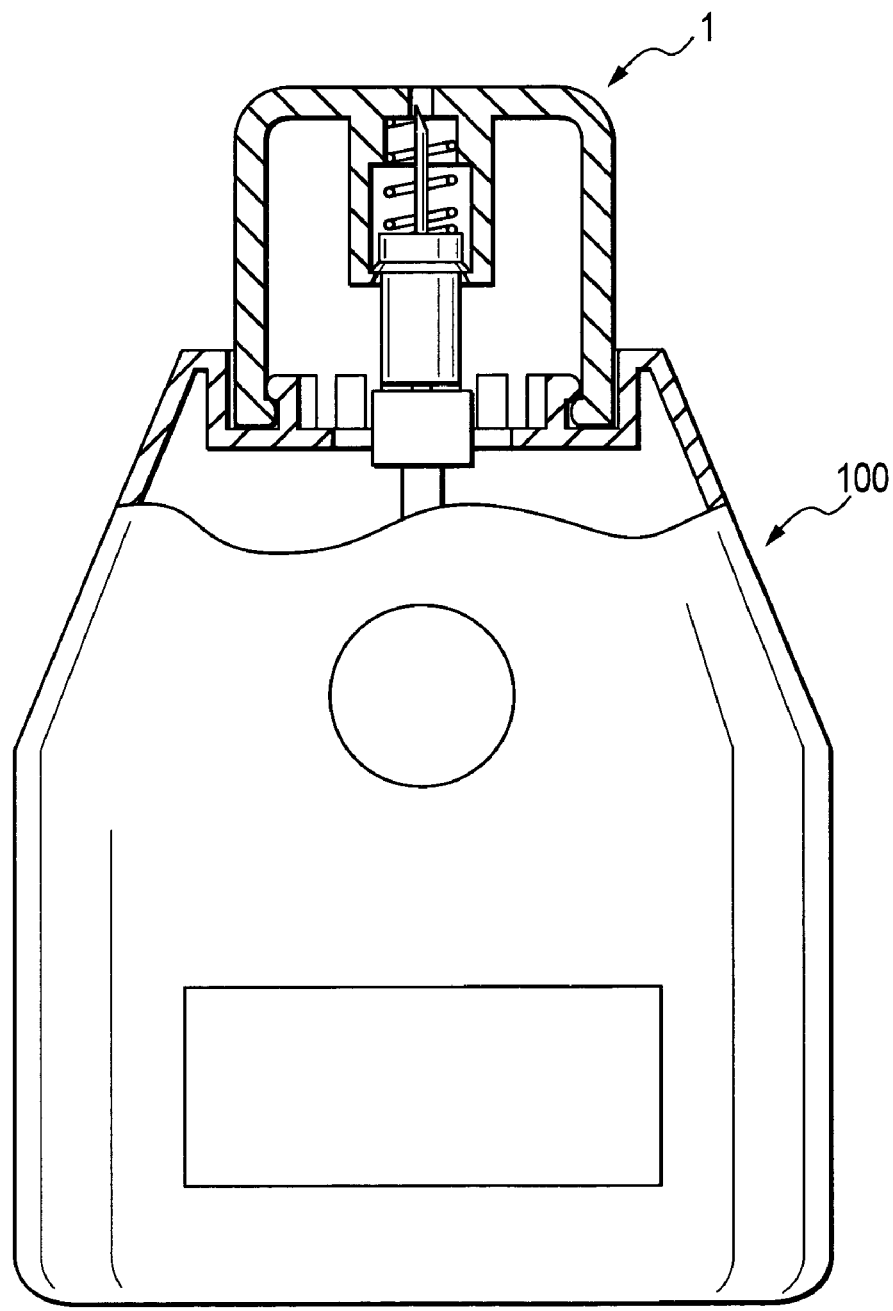
FIG. 11 shows a side view of the cap and testing device shown in FIG. 9 after the cap is installed or mounted to the testing device. The electrical contacts of the testing device are not shown.
Figure 12:
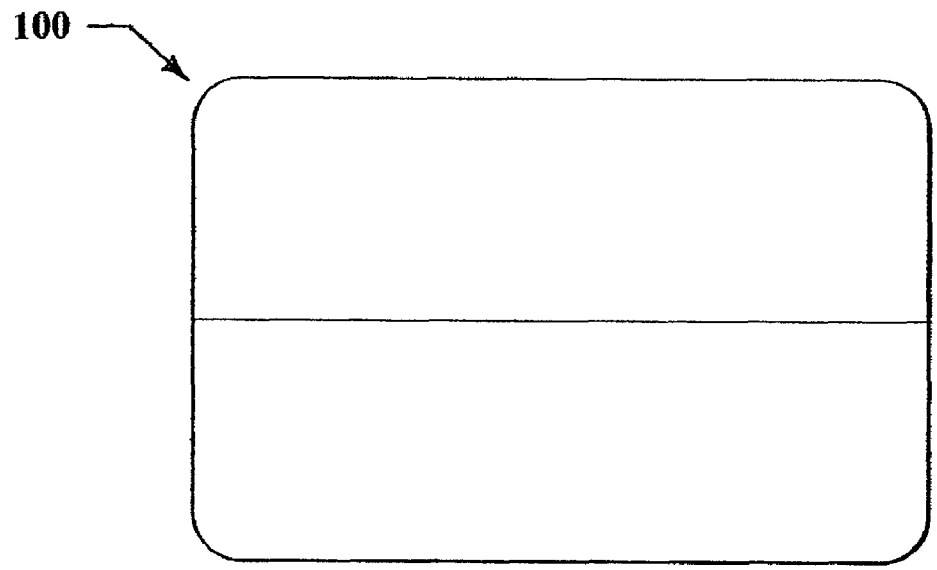
FIG. 12 shows a bottom view of the testing device shown in FIG. 11.
Figure 13:
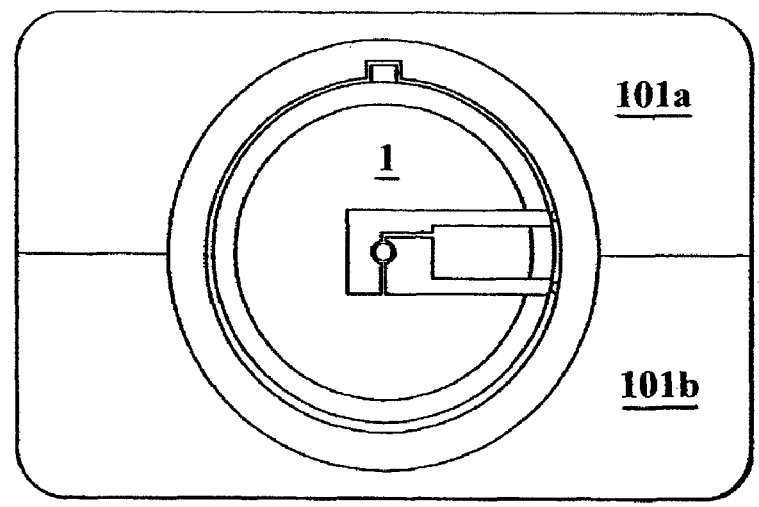
FIG. 13 shows a top view of the testing device shown in FIG. 11.

As can be seen in FIGS. 10*a* and 10*b*, the cap 1 and the testing device preferably include an alignment system which has the form of a mechanism 7 on the cap 1 and a recess 109 on the testing device 100. The alignment system ensures that the cap 1 is correctly installed on the testing device 100 so that the contacts 6*a*2 and 6*b*2 line up with and make electrical contact with electrical contacts 110*a* and 110*b* of the testing device 100. By way of non-limiting example, the body 101 of the testing device can be a two-piece body formed by an upper housing part 101*a* and a lower housing part 101*b*. These body parts can be made by, e.g., injection molding, and can be joined together by any desired connection system such as bonding, snap connection, fasteners, etc. FIGS. 11 and 13 show the cap 1 fully installed onto the testing device 100 and ready to be triggered. As can bee seen, the projection 4*a* has moved axially past the projection 106 to cause the cap 1 to be temporarily locked to the testing device 100. This occurred when the cap 1 was forced onto the testing device 100 thereby forcing the fingers containing the projection 106 to deflect inwardly. Once the projection 4*a* moved past the projection 106, their natural elasticity or memory caused them to move back to non-stressed or relaxed position. In order to remove the cap 1 from the testing device 100, however, one need only grip the cap 1 and pull it away from the testing device 100 until the projection 106 releases engagement with the projection 4*a*.

Figure 14:
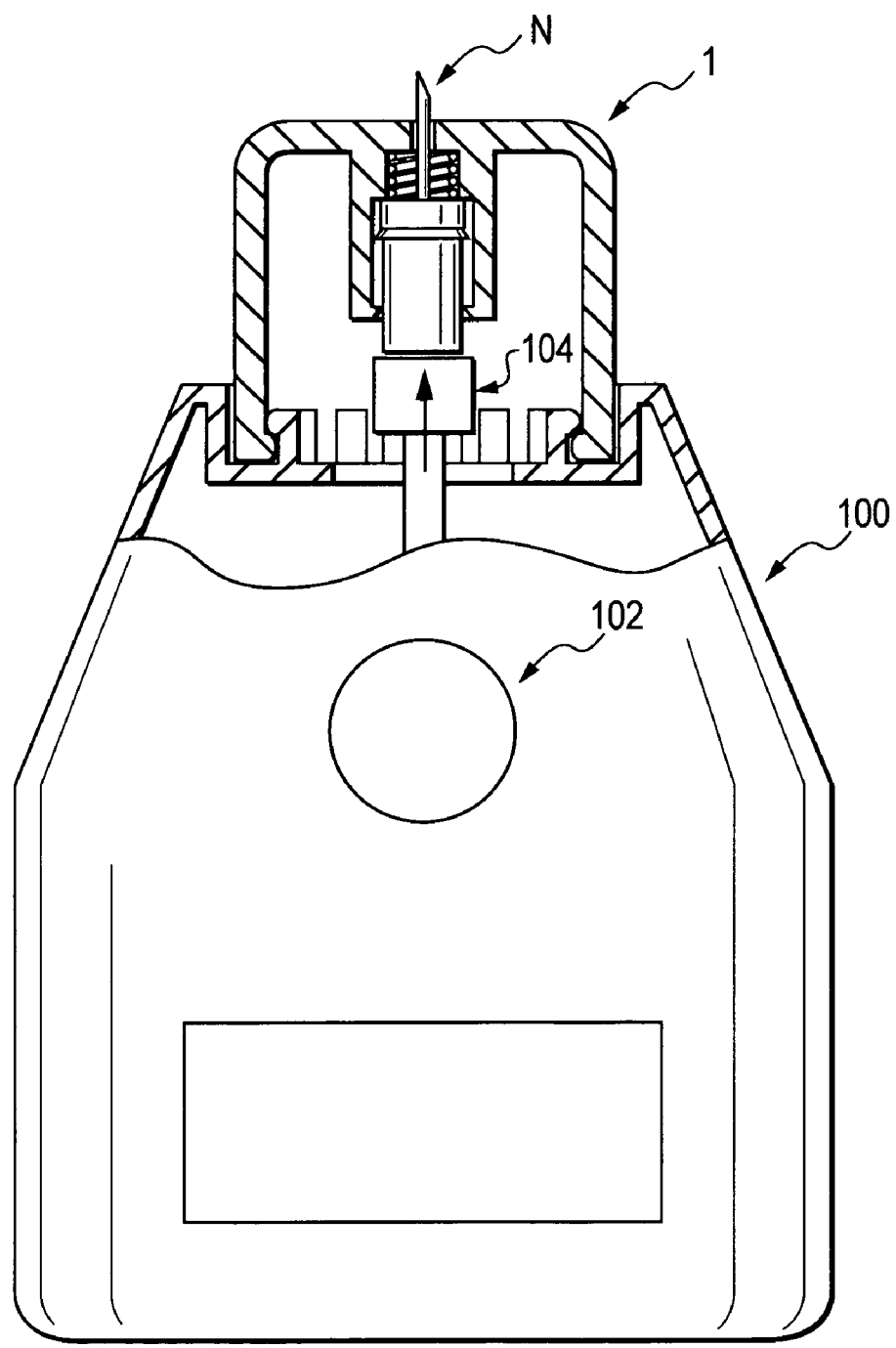
FIG. 14 shows a side view of the testing device shown in FIG. 11 after the testing device has been triggered. Triggering of the testing device has caused the lancet to move to the extended position and compress the spring. The electrical contacts of the testing device are not shown.

FIG. 14 shows the plunger 104 engaging with the lancet L thereby causing it to move to the extended position. The testing device 100 is designed so that once the plunger 104 moves to the extended position it is automatically retracted, which then allows the spring S to cause the lancet L to automatically retract. By way of non-limiting example, the testing device 100 can include an electrical actuator such as a solenoid to cause movement of the plunger 104, in which case the trigger button 102 can function as an electrical switch which causes activation of the solenoid and the plunger 104 when depressed. Alternatively, the trigger button 102 can be a mechanical device which releases the plunger 104 from a retracted position so a spring (not shown) which has been previously compressed by the plunger 104 can cause the plunger 104 to more to the extended position, and thereby cause movement of the lancet L. In this regard, the testing device 100 can include an arrangement for arming the plunger 104 similar to the one disclosed in U.S. Pat. No. 6,156,051, the disclosure of which is hereby expressly incorporated y reference in its entirety. As explained above, once the testing device 100 is triggered and the lancet L moves to the extended position, and then to the retracted position (which happens within a fraction of a second as is the case with conventional lancet devices), the plunger 104 assumes the position shown in FIG. 11. Thereafter, the testing device 100 produces a value indicative of an aspect (i.e., blood glucose) the blood or fluid sample which flows onto the contacts 6a1 and 6b1. After that, the user can simple remove the cap 1 from the testing device 100 as described above, and discard or properly dispose of it. The user can then install a new cap 1 on to the testing device 100 for use at another time or for use by another user.

Figure 15:
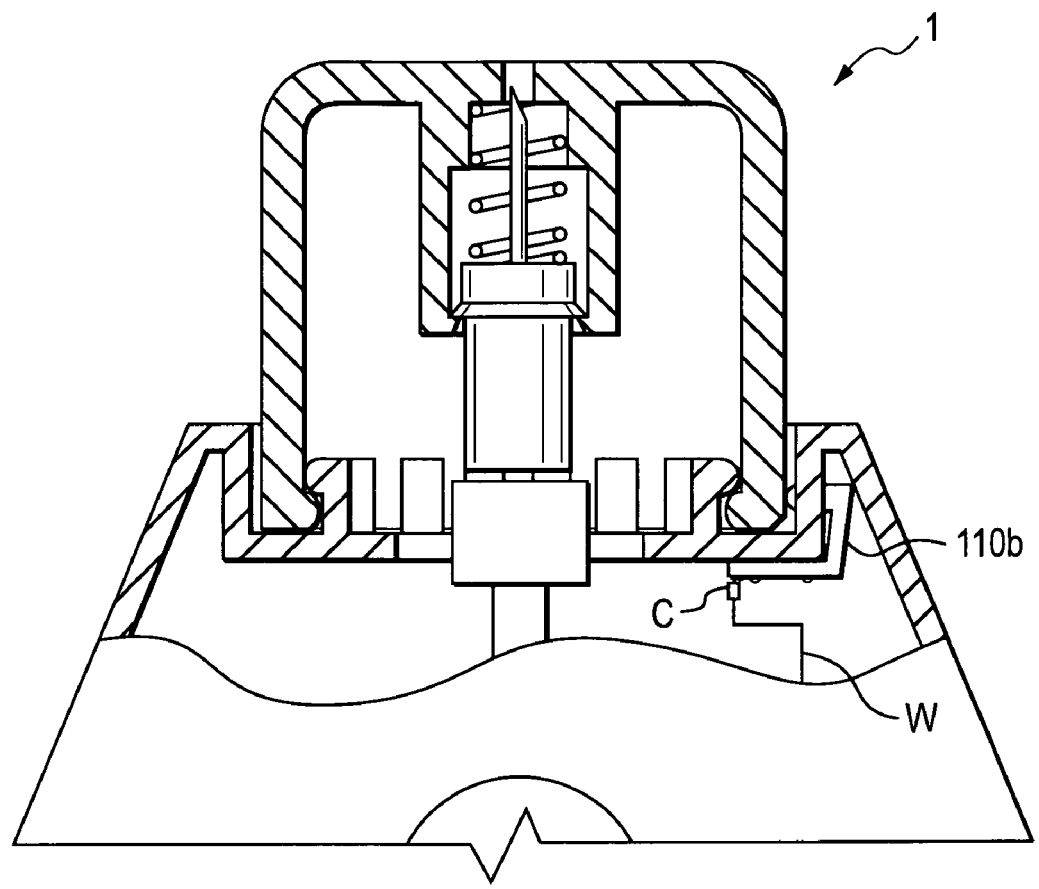
FIG. 15 shows an enlarged partial view of FIG. 14 and illustrates one non-limiting way in which the electrical contact members can be arranged on the testing device.
Figure 16:
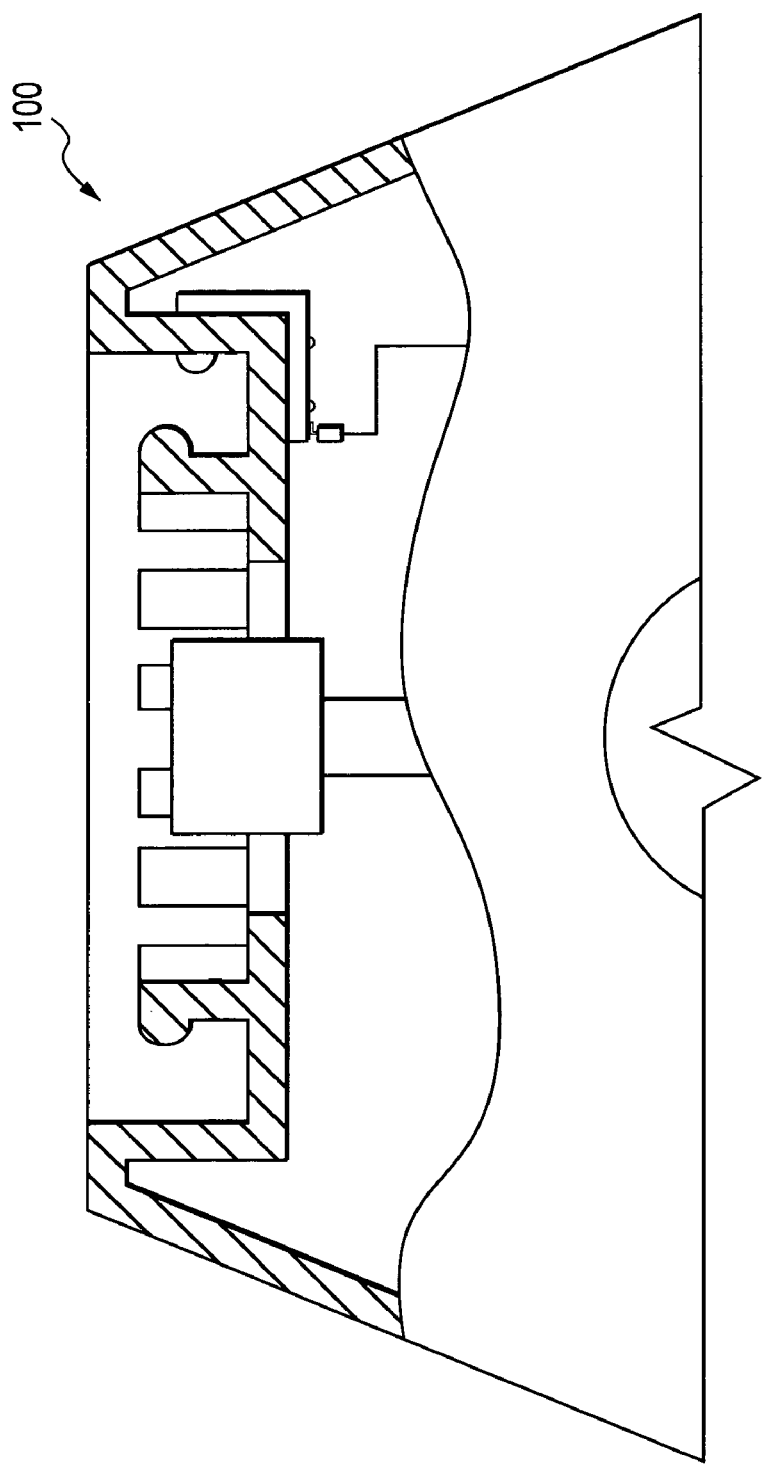
FIG. 16 shows an enlarged partial view of FIG. 15 with the cap removed to more clearly illustrate the mounting of the electrical contact members to the testing device.
Figure 17:
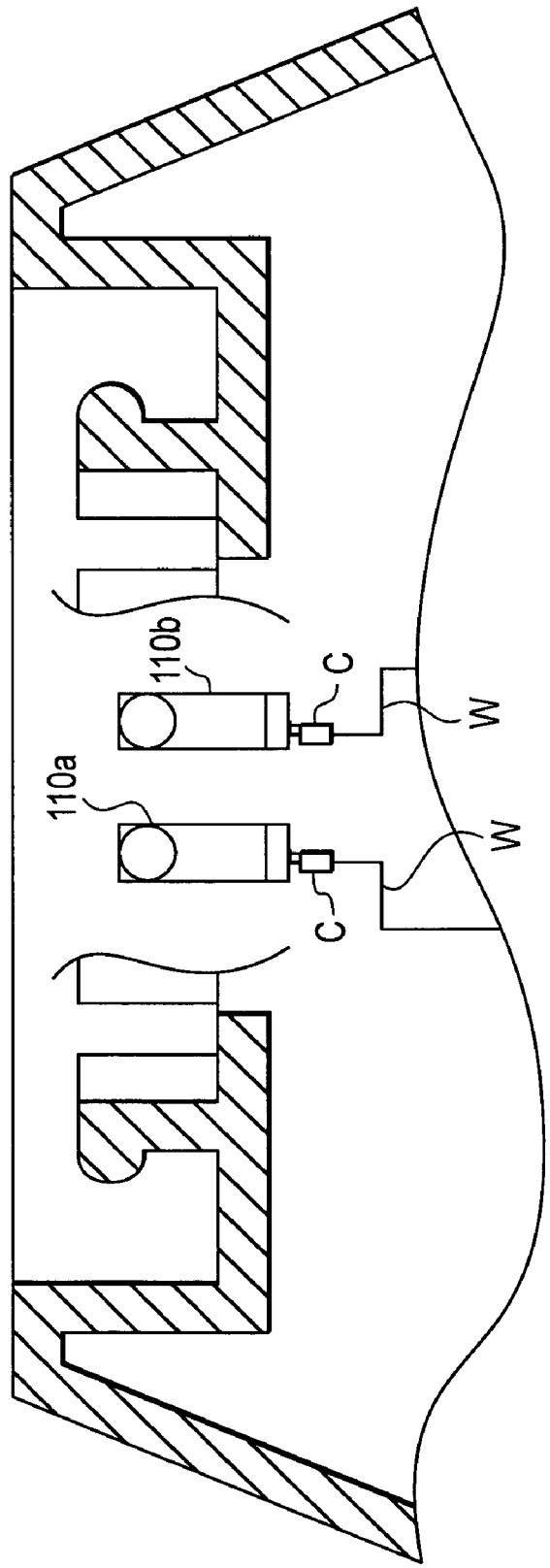
FIG. 17 shows a view similar to FIG. 16 but rotated 90 degrees. A portion of the testing device has been removed to more clearly illustrate the positioning of the electrical contact members in the testing device.
Figure 18:
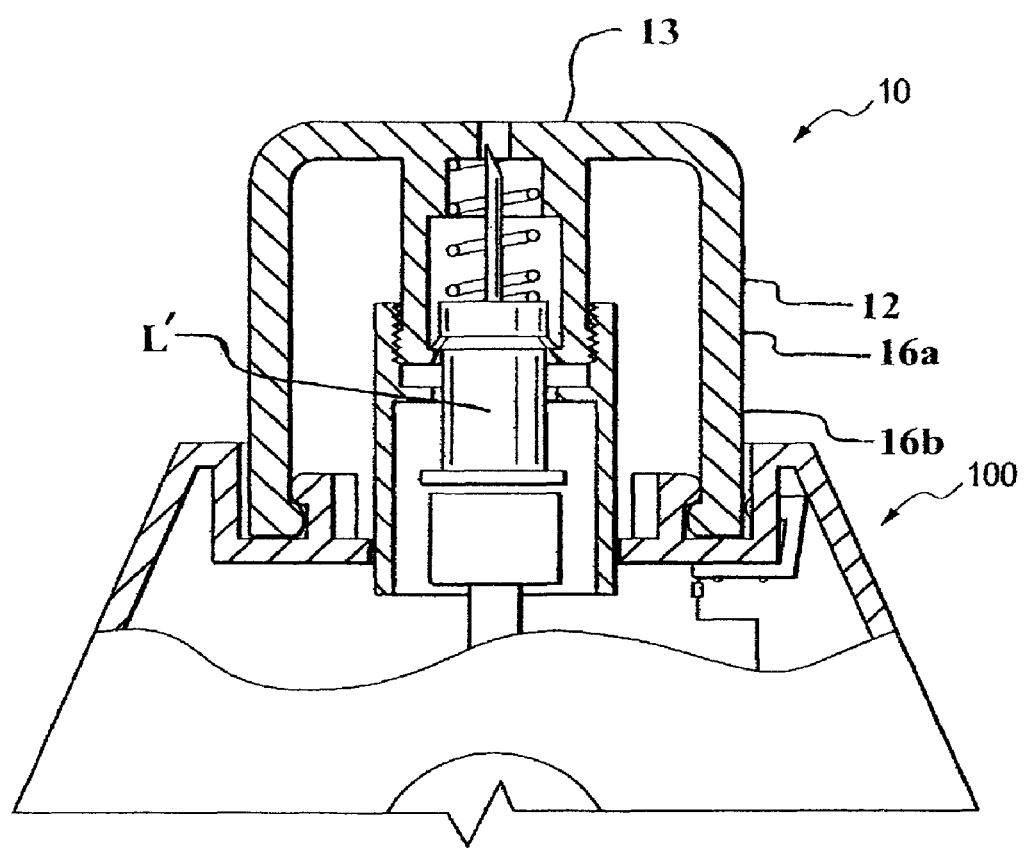
FIG. 18 shows a partial view of the testing device previously illustrated but utilizing another non-limiting embodiment of the cap which is shown in FIGS. 19-21.

FIGS. 15-17 show one non-limiting way in which the test strip of the cap 1 can make electrical contact with the testing device 100. As explained above with regard to FIG. 10b, the contacts 110a and 110b make electrical contact with the exposed contact ends 6a2 and 6b2. The contacts 110a and 110b are have a portion that is connected to the wall 107 and another end that which includes a generally spherical contacting portion. This latter spherical portion extends through an opening formed in the body 101 and into the region 105. As is evident from FIG. 15, once the cap 1 is installed onto the testing device 100 the spherical portions are caused to move into the body 101. Thus, the contacts 110a and 110b act like springs so as to make contact with the test strip of the cap 1 at all times when the cap 1 is installed onto the testing device 100. To facilitate insertion of the cap 1 and proper displacement of the contacts 110a and 110b, the end 4 of the cap 1 can preferably have a small chamfer opposite the projection 4a. Once the cap 1 is removed, however, the contacts 110a and 110b can assume a relaxed position and extend back into the region 105 (see FIG. 16). To ensure that each contact 110a and 110b communicates or is in electrical contact with the appropriate circuits in the testing device 100, a wire W from the circuit(s) is connected to each contact 110a and 110b via a connector C.

Figure 19:
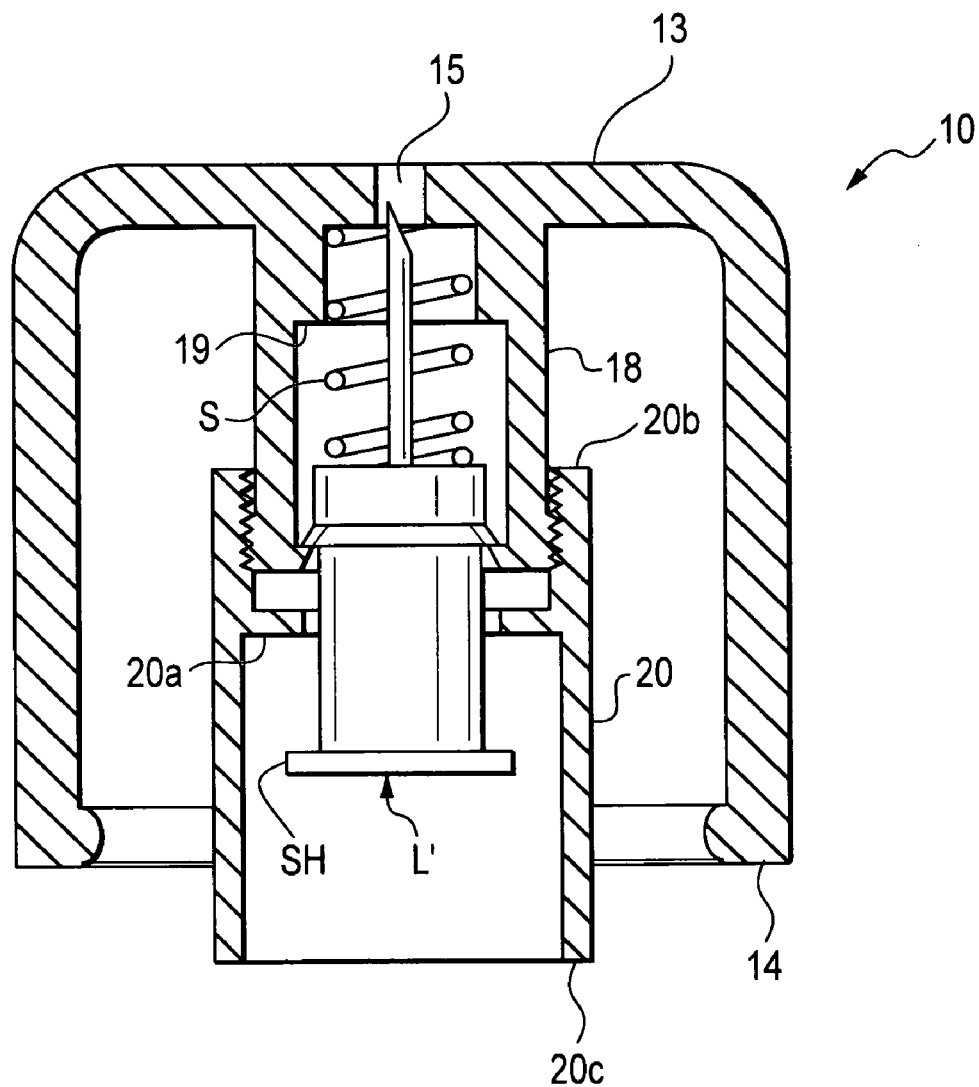
FIG. 19 shows a cross-section view of the non-limiting embodiment of the cap illustrated in the embodiment shown in FIG. 18. The cap is similar to the cap described previously but further includes a depth adjustment system to control the depth of penetration of the lancet needle. In the position shown in FIG. 19, the lancet needle will penetrate a greater amount than in the position shown in FIG. 20.
Figure 20:
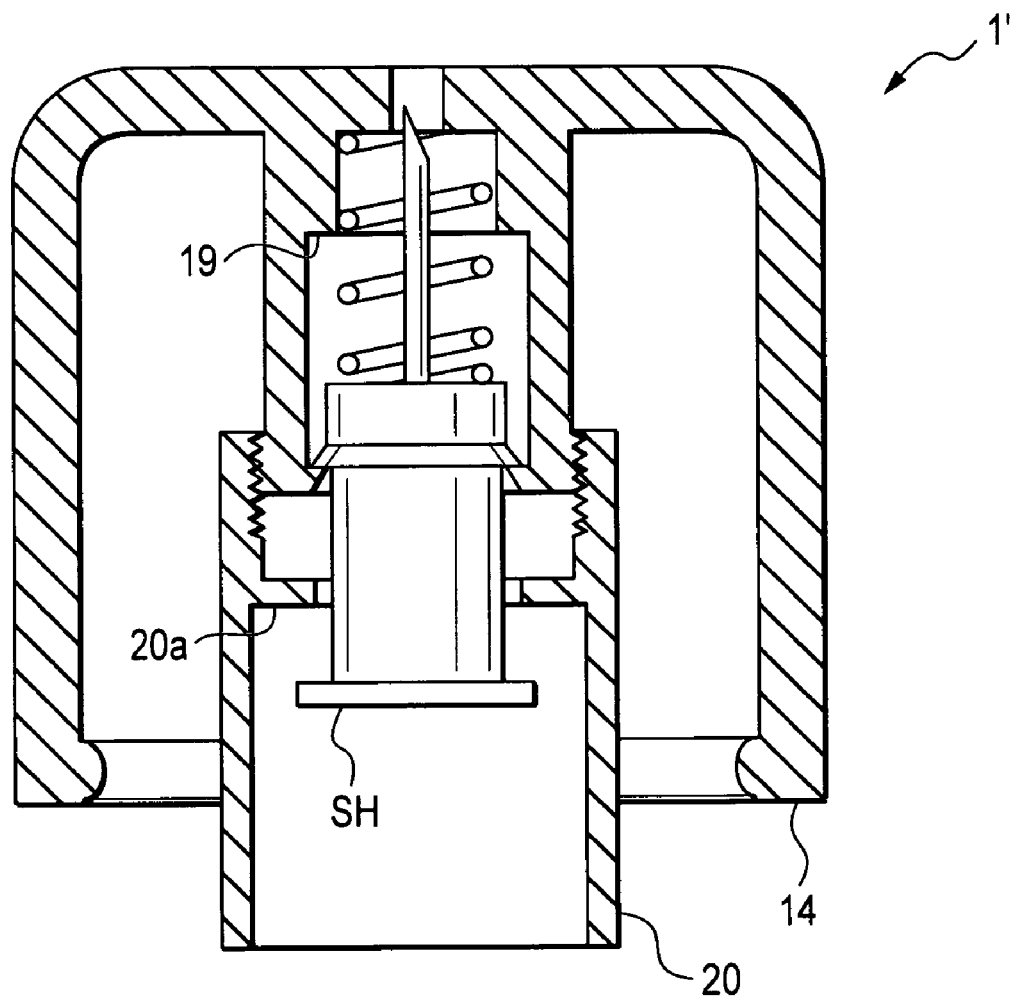
FIG. 20 shows the embodiment of FIG. 19 after the depth adjustment system is positioned at a different position. In the position shown in FIG. 20, the lancet needle will penetrate a lesser amount than in the position shown in FIG. 19.
Figure 21:
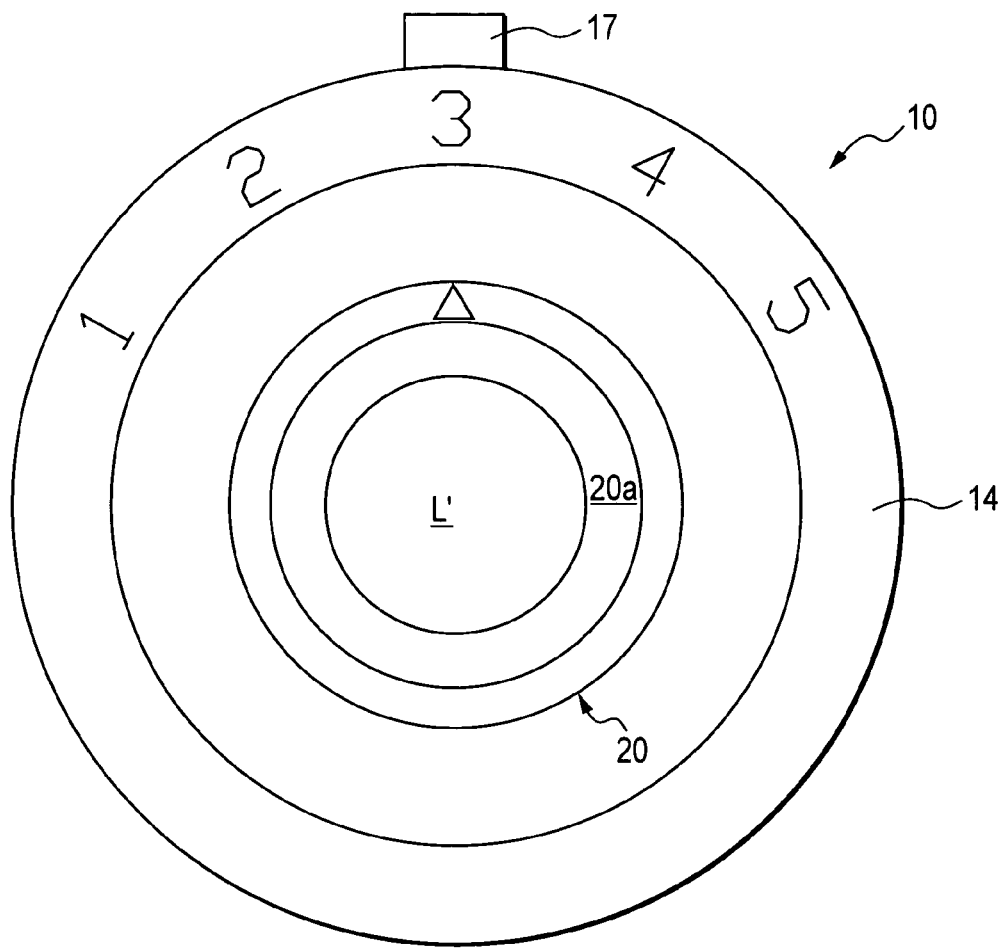
FIG. 21 shows a bottom view of depth adjustment system of the cap. The surrounding portion of the cap has not been shown for purposes of illustration.
Figure 22:
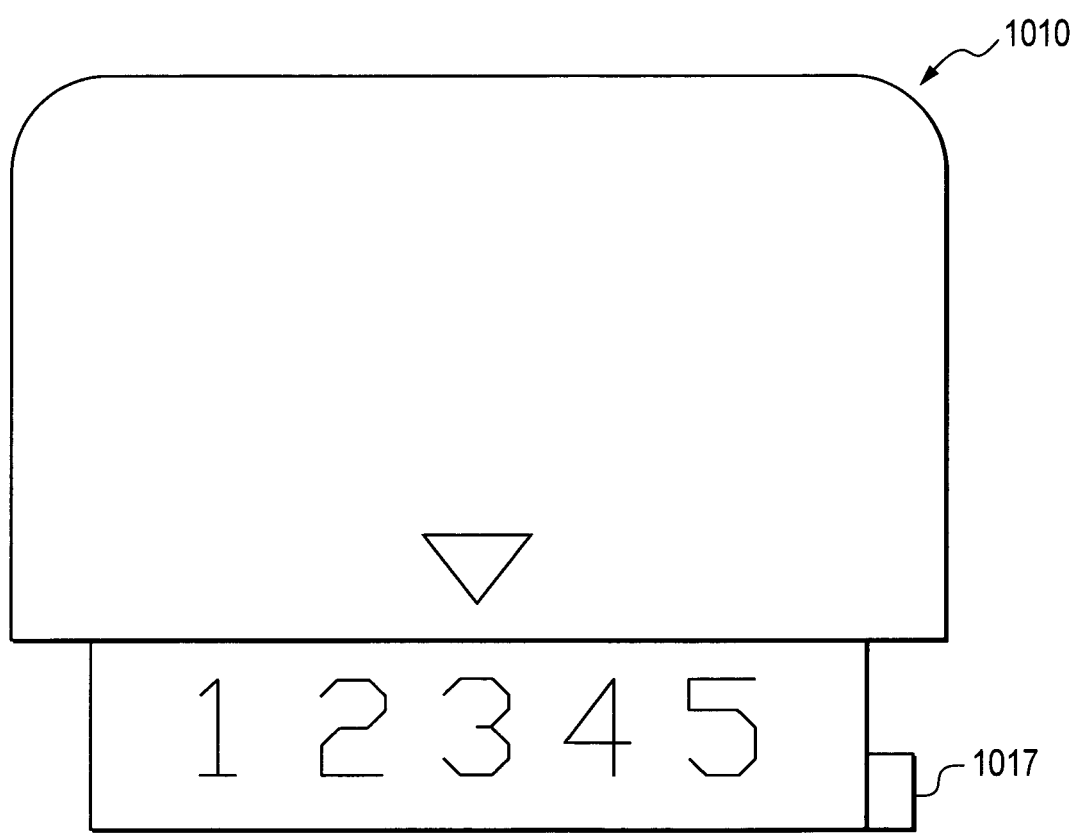
FIG. 22 shows a side view of still another non-limiting embodiment of the cap.

FIGS. 18-21 show another non-limiting embodiment of a cap 10 which includes an integral lancet L' and test strip, and which can be used with the testing device 100. Corresponding reference numbers have been increased by a factor of ten. The cap 10 is similar to the cap 1 of the previous embodiment, but additionally includes a depth adjustment system or arrangement. The cap 10 has a generally cylindrical shape including a generally cylindrical side wall 12 which extends between a skin-engaging wall 13 and an open end 14. The skin-engaging wall 13 includes an opening 15 which is sized to allow a needle N to pass therethrough. The cap 10 also includes a test strip which is at least partially arranged on an outer surface of the cap 10 as in the embodiment of FIG. 1. The test strip includes contacts 16a and 16b as in the embodiment of FIG. 1 As can be seen in FIGS. 19 and 20, the depth adjustment system comprises a generally cylindrical inner sleeve 20 which includes an upper end 20b, a shoulder section 20a and a bottom end 20c. The upper end 20b includes an internally threaded section which threadably engages with external threads arranged at a lower area of the inner housing wall 18. The shoulder 20a is designed to be contacted by a shoulder SH of the lancet L'. This contact determines the amount of the needle N which projects past the skin-engaging surface 13. As can be seen when comparing FIGS. 19 and 20, rotation of the sleeve 20 relative to the cap 10, changes the position of the shoulder 20a relative to the shoulder 19. Thus, in the position shown in FIG. 19, the shoulder SH may contact shoulder 20a in order to set the depth of penetration of the needle N. However, to the extent that the sleeve 20 is rotated to too great an amount, the depth of penetration will instead be set by contact between an upper surface of the lancet L' and the shoulder 19. This ensures that the user will not be able to set the depth of penetration too deep. In the position shown in FIG. 20, the shoulder 20a is set farther away from the shoulder 19 to as to ensure that the needle N will penetrate less deeply. This occurs because the shoulder SH contacts the shoulder 20a sooner in its travel within the inner housing. FIG. 21 shows one non-limiting way in which the user can be informed of the particular depth adjustment. According to this embodiment, the bottom end 14 of the cap 10 includes text or other indicia and the bottom end of the sleeve 20 includes a reference indicator such as, e.g., an arrow. In this way, when the user rotates the sleeve 20 relative to the cap 10, the user will know what the depth of penetration of the needle N. Thus, for example, if the arrow is aligned with the number 1 on the cap 10, the needle N will penetrate a lesser amount than when the sleeve 20 is rotated until the arrow is set reference number 2, and so on, with reference number 5 providing the deepest setting. Of course, the invention contemplates that the arrow can be provided on the surface 14 and the text on the sleeve 20. Alternatively, other text can be utilized instead of numbers such as, e.g., letters or other designations symbols. In order to ensure that the depth setting is maintained, the cap 10 and also include a circumferential projection which engages with a plurality of circumferential recesses (not shown). Such arrangements are known in the art of lancet devices and ensure that the device produces a clicking sound when rotated between depth setting positions. The cap 10 also includes a projection 17 for ensuring that the cap 10 is installed onto the testing device in only a single position as was similarly shown in the embodiment of FIG. 1.

Figure 23:
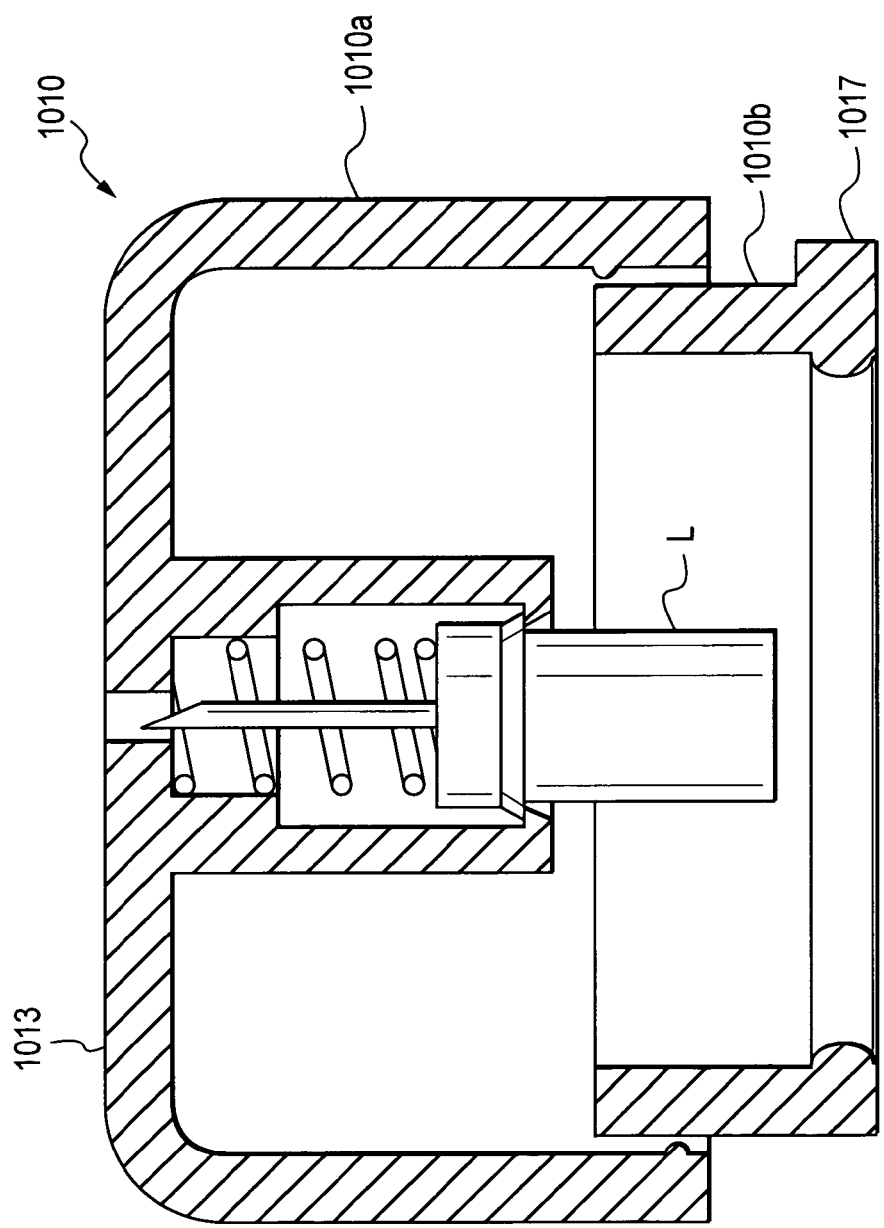
FIG. 23 shows an enlarged cross-section view of the cap shown in FIG. 22. The external thread of the lower cap member is not shown.
Figure 24:
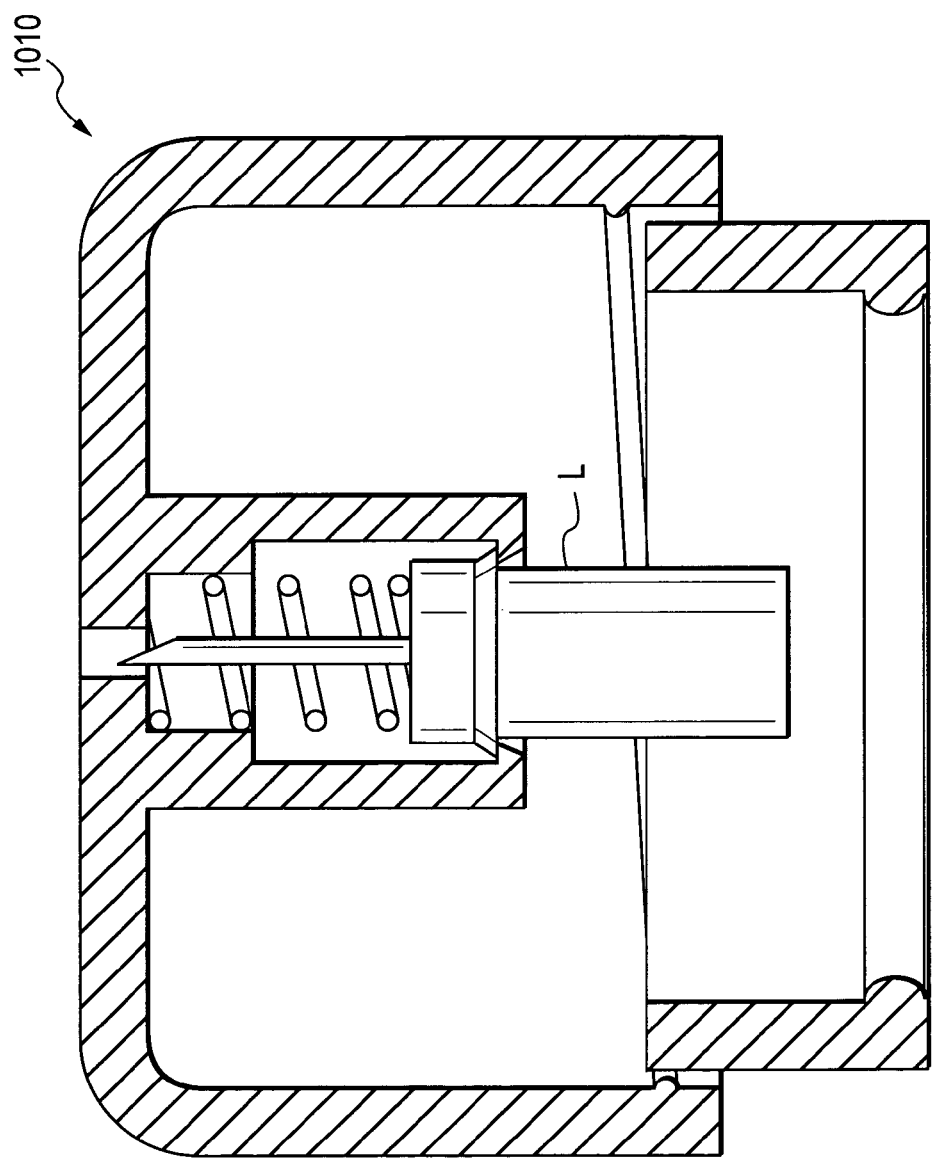
FIG. 24 shows a view similar to FIG. 23 after the bottom portion of the cap has been moved or rotated to one of many possible depth adjustment positions. The external thread of the lower cap member is not shown.
Figure 25:
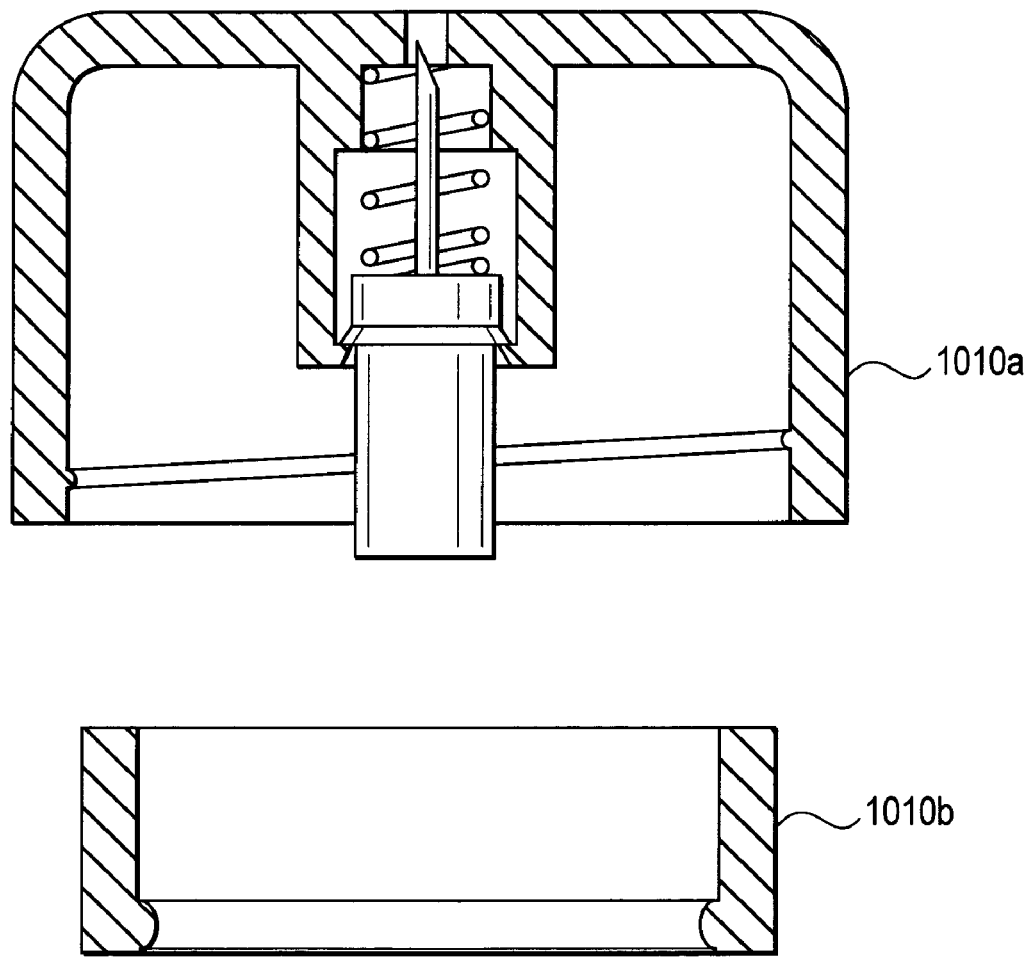
FIG. 25 shows the cap illustrated in FIG. 24 prior to the bottom portion being assembled and/or threaded onto the top portion of the cap. The external thread of the lower cap member is not shown.

FIGS. 22-25 show another non-limiting embodiment of a cap 1010 which includes an integral lancet L and test strip, and which can be used the testing device 100. Corresponding reference numbers have been increased by a factor of a thousand. The cap 1010 is similar to the cap 1 of the previous embodiment, but additionally includes a depth adjustment system or arrangement. As can be seen in FIGS. 23 and 24, the depth adjustment system comprises a generally cylindrical upper cap member 1010a which is threadably engaged with a generally cylindrical lower cap member 1010b. The upper member 1010a includes an internally threaded lower section which threadably engages with external threads arranged at an upper area of the lower member 1010b. This depth adjustment system is designed for use on a testing device which utilizes a plunger that travels a set amount. Thus, by rotating the member 1010a relative to the member 1010b one can change the position of the surface 1013 relative to the maximum movement of the plunger of the testing device. As was the case with the previous embodiment, the cap 1010 can utilize indicia and an arrow to indicate the depth adjustment.

Figure 26:
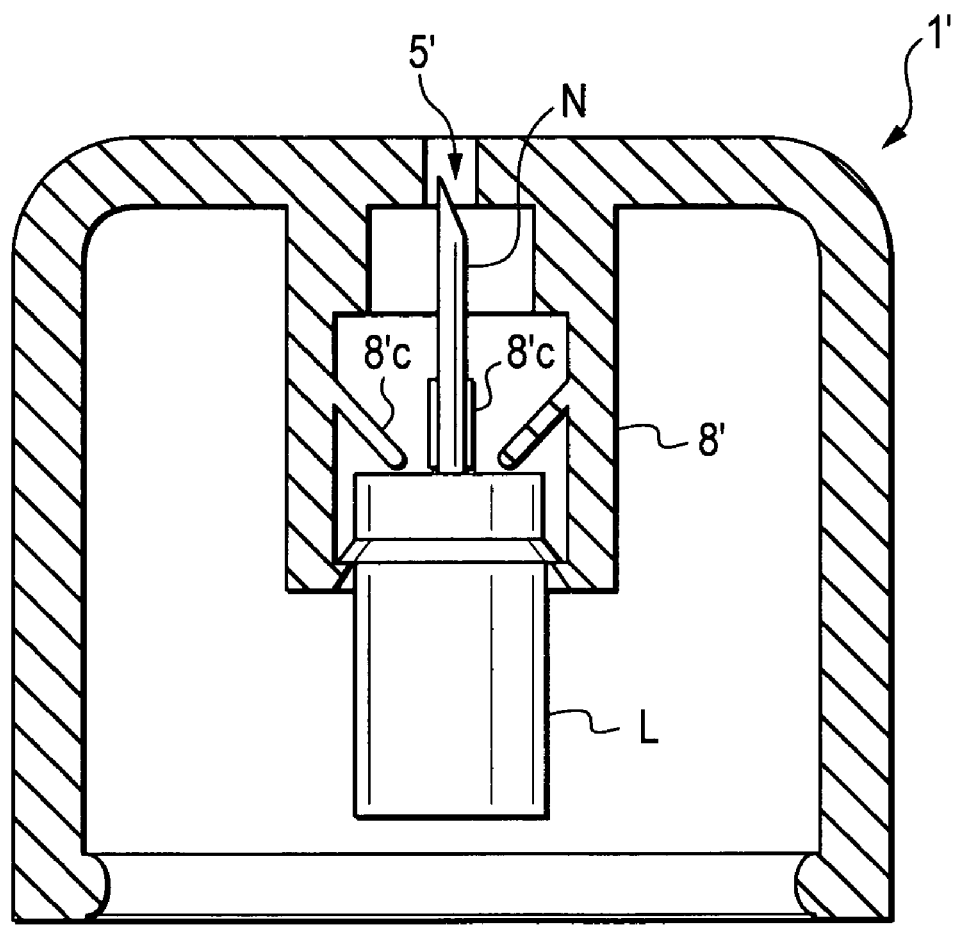
FIG. 26 shows a cross-section view of still another non-limiting embodiment of the cap. In this embodiment, the spring is replaced with integrally formed protruding members which are each connected to the cap by a living hinge.

FIG. 26 shows a cross-section view of still another non-limiting embodiment of the cap 1'. This embodiment is similar to the embodiment shown in FIGS. 1-8, except that the spring is replaced with integrally formed protruding members 8'c which are each connected to and/or integrally formed with the inner wall 8' of the cap 1' by a living hinge. As was the case with the embodiment shown in FIGS. 1-8, the fingers 8'c (instead of the spring) bias the lancet L towards a retracted position and ensure that the lancet L automatically moves to the retracted position after being moved to the extended position by the plunger of the testing device.

Figure 27:
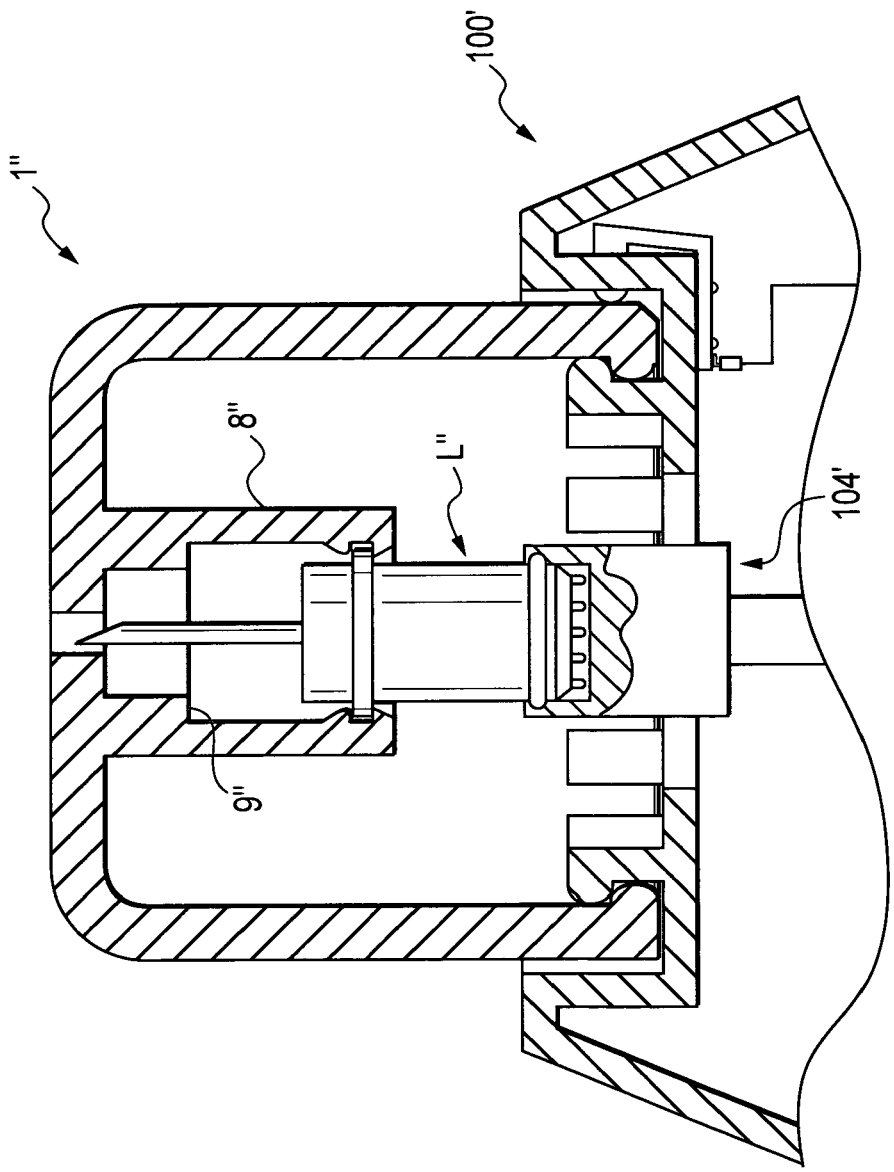
FIG. 27 shows a partial enlarged cross-section view of another non-limiting embodiment of a testing device and cap. The testing device is similar to the one used in the embodiment shown in FIG. 11 except that the plunger on the instant embodiment contains an arrangement for removably connecting to the lancet. The cap is similar to the one shown in FIGS. 1-4 except that the inner cylindrical lancet receiving housing contains an arrangement for securely retaining the lancet in the retracted position in order to ensure that the lancet connects to the plunger of the testing device. The cap of this embodiment does not need a spring or other lancet biasing devices.
Figure 28:
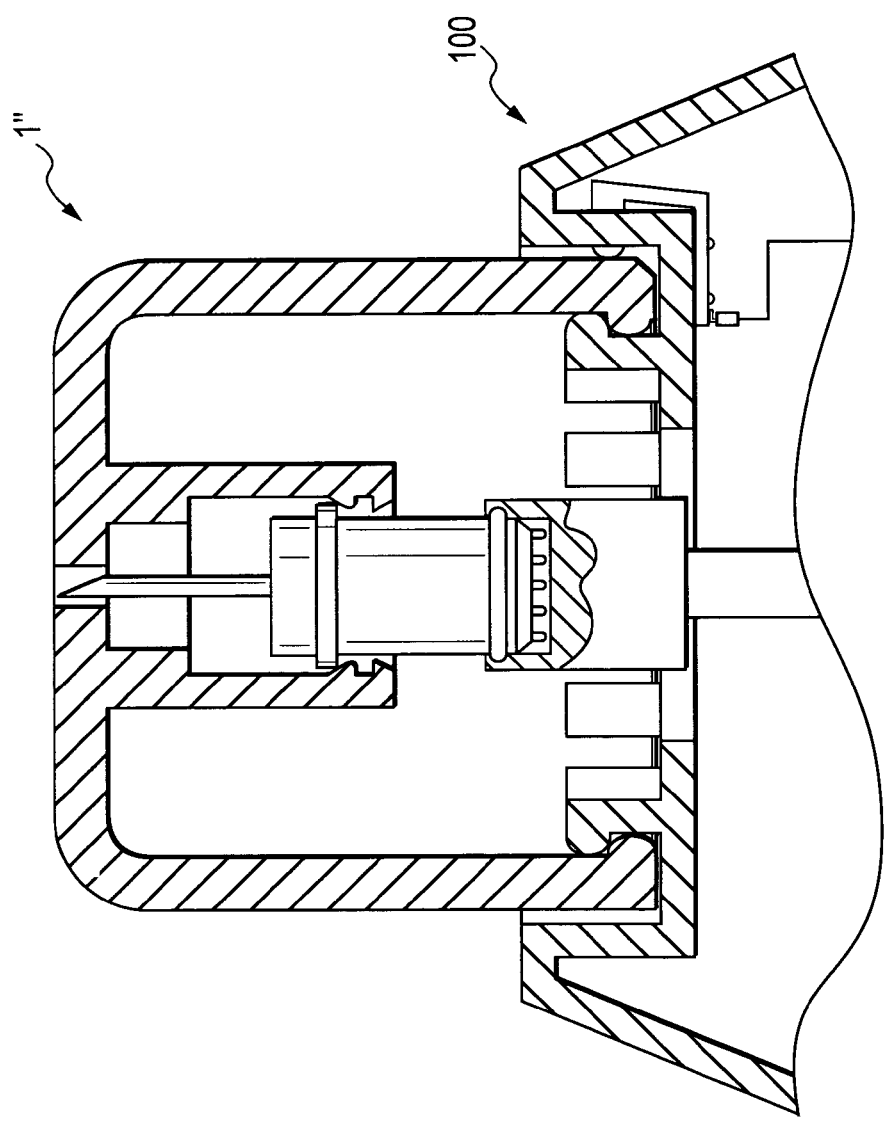
FIG. 28 shows the embodiment of FIG. 27 after the testing device has been triggered. Triggering of the testing device causes the lancet to break free from the retaining arrangement of the inner cylindrical lancet housing. In this embodiment, the penetration depth is adjusted electronically by setting the length of travel of the plunger. Once triggered, the cap can be removed from the testing device. The removal causes the lancet to move back to the retained position shown in FIG. 27 prior to the lancet being disconnected from the plunger.

FIGS. 27 and 28 show another non-limiting embodiment of a cap 1" and testing device 100'. The testing device 100' is similar to the one used in the embodiment shown in FIG. 11 except that the plunger 104' of the instant embodiment contains an arrangement for removably connecting to the lancet L". The cap 1" is similar to the one shown in FIGS. 1-4 except that no spring is utilized and the inner cylindrical lancet receiving housing or wall 8" contains an arrangement for securely retaining the lancet L" in the retracted position in order to ensure that the lancet L" connects to the plunger 104' of the testing device 100'. The cap 1" relies on plunger 104' to automatically move the lancet L" to the retracted position after being triggered instead of a spring or other lancet biasing devices. However, the invention also contemplates using a spring or integrally formed biasing fingers with this cap embodiment. In use, the cap 1" is initially installed onto the testing device 100' so that the lancet L" snaps into the plunger 104'. Once the testing device 100' is triggered, the lancet L" is caused to disengage from the inner housing or wall 8" and allowed to move to the extended position until the lancet L" contacts the shoulder 9". The plunger 104' then moves back to the retracted position, but not completely so. The lancet L" is not made to locked to the wall 8" as shown in FIG. 27. However, when the user desires to remove the cap 1" from the testing device 100', the user will pull off the cap 1" thereby forcing the lancet L" to snap back into the fully retracted position/locked position shown in FIG. 27. This ensures that the used lancet L" will not move within the housing during removal thereby providing a level of safety to the user. This arrangement occurs because the lancet L" is secured to the plunger 104' by greater frictional resistance that to the locking mechanism of the wall 8". Further pulling of the cap 1", however, will also cause the lancet L" to also disengage from the plunger 104', thereby allowing the user to remove and discard the cap 1" after use. The lancet L" is locked to the plunger 104' by way of spring fingers and slots (similar to that of the wall 8 in FIG. 7) which releasably engage with a circumferential projection of the lancet L". Of course, other releasable connection arrangements can be provided between the lancet L" and the plunger 104'.

FIG. 28 shows the testing device/cap of FIG. 27 after the testing device 100' has been triggered. Triggering of the testing device 100' causes the lancet L" to break free from the retaining arrangement of the inner cylindrical lancet housing wall 8". In this embodiment, the penetration depth is adjusted electronically by setting the length of travel of the plunger 104'. Once triggered, the cap 1" can be removed from the testing device 100'. The removal causes the lancet L" to move back to the retained position shown in FIG. 27 prior to the lancet L" being disconnected from the plunger 104'. Although not shown, this embodiment can also utilize a depth adjustment system of the type shown in FIGS. 18-25.

Figure 29C:
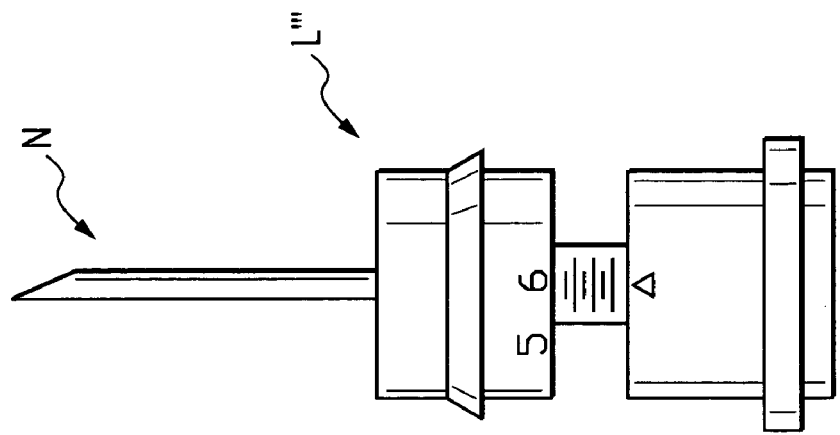
FIGS. 29a-29c shows another non-limiting embodiment of a lancet which can be used on the cap embodiment shown in, e.g., FIGS. 1-4. The lancet is designed to itself provide penetration depth adjustment. In the lowered position shown in FIG. 29a, the depth of penetration of the needle is lower than in the intermediate position shown in FIG. 29b, and depth of penetration of the needle shown in FIG. 29b is lower than in the higher position shown in FIG. 29c.
Figure 29B:
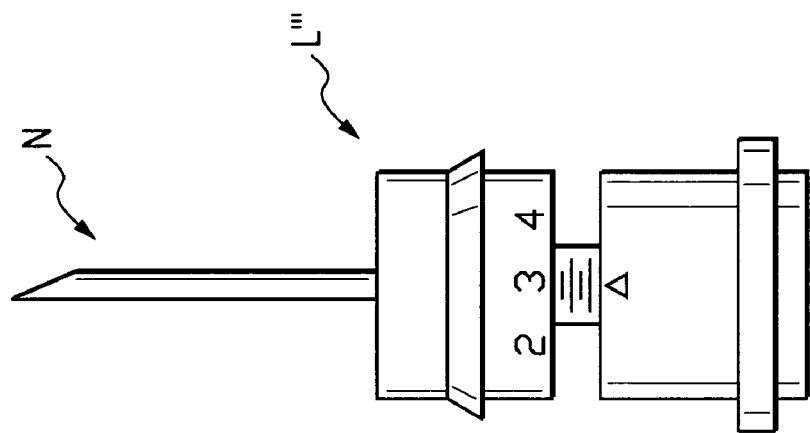
Figure 29A:
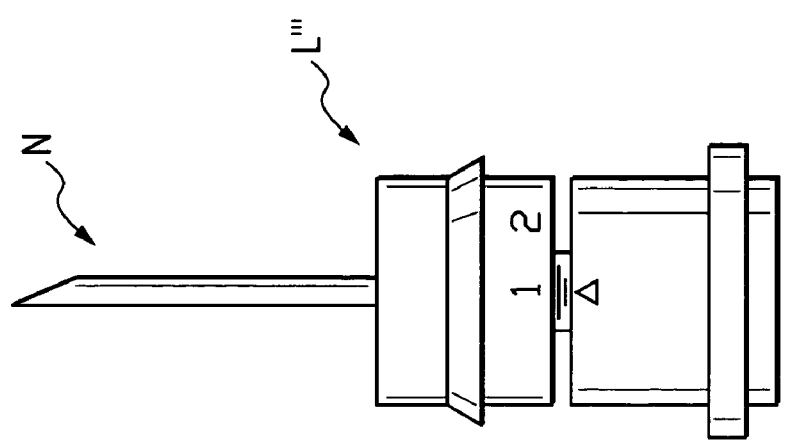

FIGS. 29a-29c shows another non-limiting embodiment of a lancet L''' which can be used on the cap embodiment shown in, e.g., FIGS. 1-4. The lancet L''' is designed to itself provide penetration depth adjustment. In the lowered position shown in FIG. 29a, the depth of penetration of the needle N is lower than in the intermediate position shown in FIG. 29b, and depth of penetration of the needle N shown in FIG. 29b is lower than in the higher position shown in FIG. 29c. The adjustment is provides by external threads arranged on a projecting portion of the lower part of the lancet L''' and by corresponding internal threads formed within an opening formed in the upper part of the lancet L'''. Indicia and an arrow can be utilized to designated to the user a desired depth setting.

Figure 30:
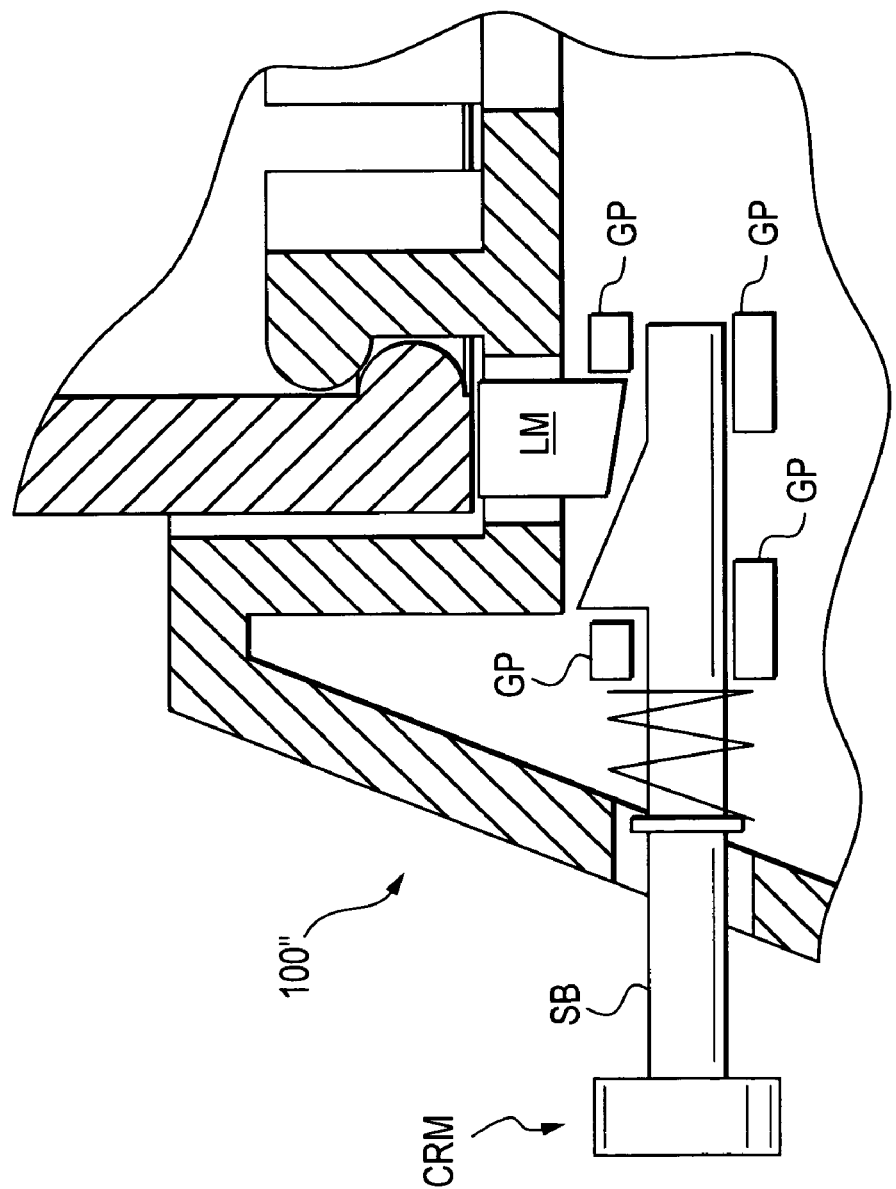
FIG. 30 shows an enlarged partial view of another embodiment of the testing device. This embodiment utilizes a mechanism for removing the cap from the testing device.

FIG. 30 shows an enlarged partial view of another embodiment of the testing device 100". Instead of allowing the user to pull off the cap from the testing device, this embodiment utilizes a cap removal mechanism CRM for more easily removing the cap (i.e., any of the cap embodiments disclosed herein) from the testing device 100". By way of non-limiting example, the mechanism CRM includes a sliding button portion SB which extends outside of the testing device 100", guiding projections GP which guide the movement of the button portion SB, a spring SP for biasing the button portion SB towards a retracted position, and a lifting member LM for lifting or moving the cap out of engagement with the testing device 100". As can be seen from FIG. 30, movement of the button SB into the testing device 100" will cause an angled upper surface to engage with a corresponding lower surface of the member LM which will, in turn, cause upward movement of the member LM thereby forcing the cap to lift out of engagement with the testing device. Although not shown, two of these mechanisms CRM may be utilized on opposite sides of the testing device 100". Of course, the invention contemplates other ways of facilitating the removal of the cap from the testing device.

The testing devices and caps disclosed herein can preferably made transparent and/or translucent synthetic resin materials. Of course, the invention is not limited to a body design which is transparent and/or translucent.

The operation of a testing device using a cap of the type described herein will now be explained with reference to the embodiment shown in FIGS. 1-17. As an initial step, the user will install the cap 1 into the mounting recess 105 of the testing device 100. This is accomplished by aligning the projection 7 and the notch 109. The user can then force the cap 1 downwards until the bottom surface 4 of the cap 1 contacts a bottom surface of the recess 105 and until there is engagement between the projections 4a and 106. The user can then begin using the testing device by switching on the testing device 100, placing, e.g., a finger, or other body part against the skin-engaging surface 3, and triggering the testing device 100 to cause the lancet needle N to puncture the finger. The user will place a blood drop on the exposed end of the test strip, i.e., on contacts 6a1 and 6b1. At this point, the device can function to automatically provide a test result after triggering and sensing the blood drop on the test strip, or upon the user manually inputting a request for testing by, e.g., pushing the trigger 102 a second time to activate the testing procedure. Once the user has received a result, the user can then manually remove the cap 1 by, e.g., pulling it off the testing device 100, or as is preferred, by activating a cap removal mechanism (see FIG. 30). This activation can also occur automatically by an actuator arranged within the testing device 100 (i.e., after a time delay) or by, e.g., the user pressing the trigger button 102 a third time. The used cap 1 can then de removed and discarded and a new cap 1 can then be installed onto the testing device 100. The device will then be ready for use again at a later time and/or by a different user.

The testing device can also be provided with a system which senses the position of the cap 1 and indicates the cap 1 is correctly installed. By way of non-limiting example, this can be accomplished using a bar-code reader system. All the parts of the cap 1, with the exception of the springs and needles (which can respectively be made of spring steel and stainless steel), may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cap for a testing device, the cap comprising:
a body having a skin-engaging end and a connecting end;
a housing arranged within the body of the cap and being disposed axially between the skin-engaging end and the connecting end;
a space arranged between the housing and the body and being disposed axially between the skin-engaging end and the connecting end;
the connecting end being configured to connect the body to the testing device;
a lancet movably mounted within the cap and comprising a proximal end, a needle projecting from the proximal end, and a distal end;
the proximal end of the lancet being disposed axially between the skin-engaging end and a distal end of the housing; and
a skin-engaging end having an opening that allows a portion of the needle of the lancet to pass therethrough.

2. The cap of claim 1, wherein the cap is structured and arranged to be removably mounted to the testing device.

3. The cap of claim 1, wherein the opening is less than approximately 10 times a diameter of the needle.

4. The cap of claim 1, further comprising an open end adapted to be removably connected to the testing device.

5. The cap of claim 1, further comprising a mechanism for ensuring that the cap is mounted to the testing device in a single rotational position.

6. The cap of claim 1, wherein the cap is structured and arranged to be non-rotationally removably mounted to the testing device.

7. The cap of claim 1, further comprising an arrangement for adjusting a depth of penetration of the needle of the lancet.

8. The cap of claim 1, further comprising a test strip having one end extending to the opening.

9. The cap of claim 1, further comprising a test strip having one end extending to the opening and another end extending along a side wall of the cap.

10. The cap of claim 1, further comprising a test strip at least partially arranged on an outer surface of the cap.

11. The cap of claim 1, further comprising a test strip having contacts arranged on a side wall of the cap.

12. The cap of claim 1, further comprising a test strip having contacts arranged in an area of the opening.

13. The cap of claim 1, wherein the cap is disposable.

14. The cap of claim 1, further comprising a mechanism for retaining the cap on the testing device.

15. The cap of claim 14, wherein the mechanism comprises a projection.

16. The cap of claim 14, wherein the mechanism comprises an inwardly facing circumferential projection.

17. The cap of claim 1, further comprising an arrangement for biasing the lancet towards a retracted position.

18. The cap of claim 17, wherein the arrangement comprises a spring.

19. The cap of claim 17, wherein the arrangement comprises at least one member connected to a portion of the cap via a living hinge.

20. The cap of claim 1, further comprising an arrangement for retaining the lancet in a retracted position.

21. The cap of claim 20, wherein the arrangement for retaining the lancet in a retracted position comprises at least one projection arranged on the lancet and at least one projection non-movably connected to the cap.

22. The cap of claim 20, wherein the arrangement for retaining the lancet in a retracted position comprises at least one projection arranged on the lancet and at least one projection integrally formed with the cap.

23. The cap of claim 20, wherein the arrangement for retaining the lancet in a retracted position comprises at least one projection arranged on the lancet and at least one projection arranged on an inner side wall of the cap.

24. The cap of claim 20, wherein the arrangement for retaining the lancet in a retracted position comprises at least one circumferential projection arranged on the lancet and at least one circumferential projection arranged on an inner cylindrical side wall of the cap.

25. A testing device comprising the cap of claim 1, the testing device comprising a body and a display.

26. A testing device comprising the cap of claim 1, the testing device comprising a body, a display, and a triggering system.

27. A testing device comprising the cap of claim 1, the testing device comprising a body, a display, and a mechanism for making electrical contact with a portion of the cap.

28. A testing device comprising the cap of claim 1, the testing device comprising a body, a display, a triggering system, and contacts for making electrical contact electrical contacts of the cap.

29. A method of puncturing a surface of skin using a testing device comprising the cap of claim 1, the method comprising:
arranging the skin-engaging end adjacent against a user's skin;
triggering the testing device so that the needle is caused to puncture the user's skin;
testing fluid from the puncture; and
removing the cap and installing a new cap on the testing device.

30. A disposable cap for a testing device, the cap comprising:
a body having a skin-engaging end and a connecting end;
the connecting end being configured to connect the cap to the testing device;
the connecting end comprising an internal member configured to releasably engage with an external member of the testing device;
a lancet movably mounted within the body and comprising a proximal end, a needle projecting from the proximal end, and a distal end;
the proximal end of the lancet being disposed axially between the skin-engaging end and the connecting end;
the distal end of the lancet being disposed axially closer to the connecting end of the body than to the skin-engaging end of the body;
an outer surface of the lancet being spaced from an inner surface of a side wall of the body;
the skin-engaging end having an opening that allows a portion of the needle of the lancet to pass therethrough; and
a test strip for testing a fluid in an area of the opening and being arranged on the body.

31. The cap of claim 30, wherein the cap is structured and arranged to be removably mounted to the testing device.

32. The cap of claim 30, wherein the opening is less than approximately 5 times a diameter of the needle.

33. The cap of claim 30, wherein the connecting end comprises an open end adapted to be removably connected to the testing device.

34. The cap of claim 30, further comprising a mechanism for ensuring that the cap is mounted to the testing device in a single rotational position.

35. The cap of claim 30, wherein the cap is structured and arranged to be non-rotationally removably mounted to the testing device.

36. The cap of claim 30, wherein the test strip is at least partially arranged on an outer surface of the cap.

37. The cap of claim 30, wherein the internal and external members are the only mechanism for retaining the cap on the testing device.

38. The cap of claim 30, further comprising an arrangement for biasing the lancet towards a retracted position.

39. The cap of claim 30, further comprising an arrangement for retaining the lancet needle in a retracted position.

40. A testing device comprising the cap of claim 30, the testing device comprising a body and a display.

41. A testing device comprising the cap of claim 30, the testing device comprising a body, a display, and a triggering system.

42. A testing device comprising the cap of claim 30, the testing device comprising a body, a display, and a mechanism for making electrical contact with the test strip.

43. A testing device comprising the cap of claim 30, the testing device comprising a body, a display, a triggering system, and contacts for making electrical contact electrical contacts of the test strip.

44. A method of puncturing a surface of skin using a testing device comprising the cap of claim 30, the method comprising:
   arranging the skin-engaging end adjacent against a user's skin;
   triggering the testing device so that the needle is caused to puncture the user's skin;
   testing fluid from the puncture; and
   removing the cap and installing a new cap on the testing device.

45. A disposable cap for a testing device, the cap comprising:
   a body comprising:
      an annular housing arranged within the body and being disposed axially between a skin-engaging end and a distal end of the body; and
      an annular space arranged between the annular housing and the body and being disposed axially between the skin-engaging end and the distal end of the body;
   a lancet having a needle projecting from a proximal end of the lancet and being movably mounted within the annular housing;
   the proximal end of the lancet being disposed axially between the skin-engaging end and a distal end of the annular housing;
   an arrangement for biasing the lancet towards a retracted position;
   the skin-engaging end having an opening that allows a portion of the needle of the lancet to pass therethrough; and
   a test strip arranged on the body for testing a fluid in an area of the opening.

46. The disposable cap of claim 45, further comprising an arrangement for changing a length of movement of the lancet.

47. The disposable cap of claim 45, further comprising an arrangement for adjusting a penetration depth of the needle of the lancet.

48. A glucose meter comprising the disposable cap of claim 45.

49. A method of testing a fluid sample using the glucose meter of claim 48, the method comprising:
   arranging the skin-engaging end adjacent against a user's skin;
   triggering the glucose meter so that the needle is caused to puncture the user's skin;
   testing fluid from the puncture; and
   removing the cap and installing a new cap on the glucose meter.

* * * * *

UNITED STATES PATENT AND TRADEMARK OFFICE
CERTIFICATE OF CORRECTION

PATENT NO.      : 8,211,036 B2
APPLICATION NO. : 11/138277
DATED           : July 3, 2012
INVENTOR(S)     : S. Schraga It is certified that error appears in the above-identified patent and that said Letters Patent is hereby corrected as shown below:

At column 14, line 22 (claim 28, line 3), please change "electrical contact electrical" with -- electrical contact with electrical --.

At column 15, line 17 (claim 43, line 3), please change "electrical contact electrical" with -- electrical contact with electrical --.

Signed and Sealed this
Twenty-ninth Day of January, 2013

David J. Kappos
*Director of the United States Patent and Trademark Office*